(12) United States Patent
Takada et al.

(10) Patent No.: US 10,647,648 B2
(45) Date of Patent: May 12, 2020

(54) METHOD FOR PURIFYING ORGANIC SOLVENT

(71) Applicant: ORGANO CORPORATION, Tokyo (JP)

(72) Inventors: Hitoshi Takada, Kanagawa (JP); Akira Nakamura, Tokyo (JP); Masami Imamura, Hyogo (JP); Koji Yamanaka, Shizuoka (JP)

(73) Assignee: ORGANO CORPORATION, Tokyo (JP)

( * ) Notice: Subject to any disclaimer, the term of this patent is extended or adjusted under 35 U.S.C. 154(b) by 2 days.

(21) Appl. No.: 16/066,202

(22) PCT Filed: Oct. 28, 2016

(86) PCT No.: PCT/JP2016/081980
§ 371 (c)(1),
(2) Date: Jun. 26, 2018

(87) PCT Pub. No.: WO2017/115550
PCT Pub. Date: Jul. 6, 2017

(65) Prior Publication Data
US 2019/0300464 A1   Oct. 3, 2019

(30) Foreign Application Priority Data

Dec. 28, 2015   (JP) .................................. 2015-256251

(51) Int. Cl.
*C07C 29/76*   (2006.01)
*B01J 39/18*   (2017.01)
(Continued)

(52) U.S. Cl.
CPC ............... *C07C 29/76* (2013.01); *B01J 39/04* (2013.01); *B01J 39/20* (2013.01); *C07C 31/10* (2013.01); *B01J 20/28042* (2013.01); *B01J 20/28085* (2013.01); *B01J 39/18* (2013.01); *B01J 47/00* (2013.01)

(58) Field of Classification Search
CPC .... C07C 29/76; C07C 31/10; B01J 20/28042; B01J 20/28085; B01J 47/00; B01J 39/18
See application file for complete search history.

(56) References Cited

U.S. PATENT DOCUMENTS 6,733,637 B1   5/2004   Burton et al.
6,951,609 B2 *  10/2005   Yamanaka ............... C02F 1/42
                                                                    210/202

(Continued)

FOREIGN PATENT DOCUMENTS

CN      102898275      1/2013
JP      2003-535836    12/2003
(Continued)

OTHER PUBLICATIONS

International Search Report in International Application PCT/JP2017/005547 dated Jan. 17, 2017.
(Continued)

*Primary Examiner* — Yate' K Cutliff
(74) *Attorney, Agent, or Firm* — Greenblum & Bernstein, P.L.C.

(57) ABSTRACT

A method for purifying an organic solvent, comprising contacting an organic solvent containing polyvalent metal ions with a monolithic organic porous ion exchanger.
According to the present invention, a method for purifying an organic solvent can be provided, wherein a high rate of removing polyvalent metal ions in an organic solvent is achieved.

6 Claims, 3 Drawing Sheets

(51) Int. Cl.
*B01J 39/04* (2017.01)
*B01J 39/20* (2006.01)
*C07C 31/10* (2006.01)
*B01J 20/28* (2006.01)
*B01J 47/00* (2017.01)

(56) References Cited

U.S. PATENT DOCUMENTS

| | | | | |
|---|---|---|---|---|
| 2011/0206569 A1* | 8/2011 | Rohde | .................. | B01J 19/2485 |
| | | | | 422/187 |
| 2011/0290714 A1* | 12/2011 | Inoue | ........................ | C08F 2/32 |
| | | | | 210/496 |
| 2015/0144557 A1* | 5/2015 | Ly | ........................ | B01D 15/361 |
| | | | | 210/638 |
| 2016/0233082 A1* | 8/2016 | Yano | .................. | H01L 21/67017 |

FOREIGN PATENT DOCUMENTS

| | | | | |
|---|---|---|---|---|
| JP | 2007-275690 | | 10/2007 | |
| JP | 2009-57286 | | 3/2009 | |
| JP | 2009067982 | A * | 4/2009 | .............. B01J 20/26 |
| JP | 2010-234356 | | 10/2010 | |
| JP | 2012-506799 | | 3/2012 | |
| JP | 2012-167062 | | 9/2012 | |
| JP | 2015-67532 | | 4/2015 | |
| JP | 2015-521101 | | 7/2015 | |
| WO | 2010/049515 | | 5/2010 | |
| WO | 2015/045975 | | 4/2015 | |

OTHER PUBLICATIONS

International Preliminary Report on Patentability in International Application PCT/JP2016/081980 dated Jul. 3, 2018.

* cited by examiner

METHOD FOR PURIFYING ORGANIC SOLVENT

TECHNICAL FIELD

The present invention relates to a method for purifying an organic solvent in order to remove polyvalent metal ions contained in the organic solvent to thereby purify the organic solvent.

BACKGROUND ART

Recently, in semiconductor manufacturing processes, isopropanol (IPA) has become used for drying semiconductor substrates after washing with water. When metal ions have mixed into IPA used for drying semiconductor substrates after washing with water, metal remains on semiconductor substrates, leading to a decrease in the yield. Thus, as IPA used for drying semiconductor substrates after washing with water, high-purity IPA having an extremely low content of metal ions is required.

In the case of carrying out solution polymerization by dissolving monomers in an organic solvent, if metal ions are present in the organic solvent, metal mixes into a polymer as a product and may be responsible for a decrease in the performance. Accordingly, also as organic solvents used as a solvent for monomer polymerization, high-purity solvents having an extremely low content of metal ions are required.

In production facilities in which a large amount of organic solvents is used for washing various materials to be cleaned, dissolution and dispersion of functional compounds, and the like, recovery and recycling of organic solvents used for washing and the like are required without discharging them outside, from the viewpoint of considering the environment. For this reason, in order to recycle recovered organic solvents, it is required to remove metal ions mixed in the solvents due to washing or the like from the recovered organic solvents.

An exemplary method for purifying an organic solvent is purification by distillation. However, distillation requires a large facility and enormous energy, leading to an increase in the purification cost.

In contrast, a method including use of a particulate ion exchange resin, specifically, purification by contacting an organic solvent with a particulate ion exchange resin as described in Patent Literature 1 or 2 below, which only requires allowing an organic solvent to pass through an ion exchange resin tower, can achieve convenient purification and keep the purification cost low, as compared with distillation.

CITATION LIST

Patent Literature

[Patent Literature 1] Japanese Patent Laid-Open No. 2009-57286
[Patent Literature 2] National Publication of International Patent Application No. 2003-535836

SUMMARY OF INVENTION

Technical Problem

The present inventors have made investigations and unfortunately have found that a purification method comprising contacting an organic solvent with a particulate ion exchange resin sufficiently removes monovalent metal ions such as sodium ions and potassium ions in the organic solvent but has a problem in that removal of polyvalent metal ions such as magnesium ions, chromium ions, and zinc ions is more difficult than removal of monovalent metal ions.

Accordingly, it is an object of the present invention to provide a method for purifying an organic solvent, wherein a high rate of removing polyvalent metal ions in the organic solvent is achieved.

Solution to Problem

In such situations, the present inventors have made intensive investigations and, as a result, have found that use of a monolithic organic porous ion exchanger can satisfactorily remove polyvalent metal ions such as magnesium ions, chromium ions, and zinc ions, removal of which has been difficult with particulate ion exchange resins, having completed the present invention.

That is, an aspect (1) of the present invention provides a method for purifying an organic solvent, comprising contacting an organic solvent containing polyvalent metal ions with a monolithic organic porous ion exchanger.

An aspect (2) of the present invention provides the method for purifying an organic solvent according to (1), wherein the monolithic organic porous ion exchanger is a monolithic organic porous cation exchanger, and the polyvalent metal ions are any one or two or more of a magnesium ion, a chromium ion, and a zinc ion.

An aspect (3) of the present invention provides the method for purifying an organic solvent according to (1) or (2), wherein the organic solvent is any one or two or more of alcohols, cellosolves, ethers, ketones, and esters, or a mixture of two or more of alcohols, cellosolves, ethers, ketones, and esters.

An aspect (4) of the present invention provides the method for purifying an organic solvent according to (1) or (2), wherein the organic solvent is isopropanol.

An aspect (5) of the present invention provides the method for purifying an organic solvent according to any of (1) to (4), wherein the monolithic organic porous ion exchanger comprises a continuous skeleton phase and a continuous hole phase, the exchanger has a thickness of a continuous skeleton of 1 to 100 μm, an average diameter of continuous holes of 1 to 1000 μm, a total pore volume of 0.5 to 50 mL/g, and an ion exchange capacity per weight in a dry state of 1 to 6 mg equivalents/g, and ion exchange groups are uniformly distributed in the organic porous ion exchanger.

An aspect (6) of the present invention provides the method for purifying an organic solvent according to (5), wherein the monolithic organic porous ion exchanger comprises an open-cell structure in which cellular macropores overlap and the overlapping macropores form openings having an average diameter of 1 to 1000 μm, the exchanger has a total pore volume of 1 to 50 mL/g and an ion exchange capacity per weight in a dry state of 1 to 6 mg equivalents/g, and ion exchange groups are uniformly distributed in the organic porous ion exchanger.

An aspect (7) of the present invention provides the method for purifying an organic solvent according to (5), wherein the monolithic organic porous ion exchanger includes a continuous macropore structure in which cellular macropores overlap and the overlapping macropores form openings having an average diameter of 30 to 300 μm, the exchanger has a total pore volume of 0.5 to 10 mL/g, and an ion exchange capacity per weight in a dry state of 1 to 6 mg equivalents/g, and ion exchange groups are uniformly distributed in the organic porous ion exchanger, and an area of a skeleton portion appearing in cross section in a SEM image of a cut section of the continuous macropore structure (dry body) is 25 to 50% based on the image area.

An aspect (8) of the present invention provides the method for purifying an organic solvent according to (5), wherein the monolithic organic porous ion exchanger includes a bicontinuous structure that comprises a three-dimensionally continuous skeleton comprising an aromatic vinyl polymer that has a crosslinked structural unit content of 0.1 to 5.0 mol % based on all constituent units including ion exchange groups introduced and having an average thickness of 1 to 60 µm, and three-dimensionally continuous holes defined by the skeleton having an average diameter of 10 to 200 µm, the exchanger has a total pore volume of 0.5 to 10 mL/g and an ion exchange capacity per weight in a dry state of 1 to 6 mg equivalents/g, and the ion exchange groups are uniformly distributed in the organic porous ion exchanger.

Advantageous Effect of Invention

According to the present invention, a method for purifying an organic solvent can be provided, wherein a high rate of removing polyvalent metal ions in an organic solvent is achieved.

DESCRIPTION OF EMBODIMENTS

Figure 1:
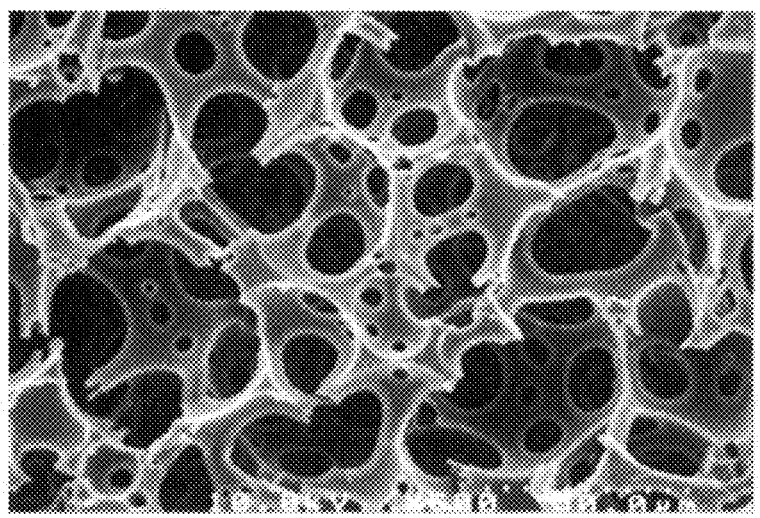
FIG. 1 is a SEM photograph of an exemplary embodiment of a first monolithic organic porous cation exchanger.

The method for purifying an organic solvent of the present invention is a method for purifying an organic solvent, comprising contacting an organic solvent containing polyvalent metal ions with a monolithic organic porous ion exchanger.

The organic solvent according to the method for purifying an organic solvent of the present invention is a target to be purified by the method for purifying an organic solvent of the present invention. Examples of the organic solvent include, but are not particularly limited to, alcohols such as methanol, ethanol, 1-propanol, 2-propanol (isopropanol: IPA), and butanol; cellosolves such as ethylene glycol monomethyl ether acetate; ethers such as ethylene glycol monomethyl ether; cyclic ethers such as tetrahydrofuran; ketones such as acetone and methyl ethyl ketone, and esters such as acetates and lactates.

As for physical properties of such an organic solvent, the relative permittivity of the organic solvent is preferably 10 to 50, particularly preferably 15 to 40. When the relative permittivity of the organic solvent is in the range described above, ions in the solvent are stabilized. Since solvation of cations proceeds electrostatically or coordinatively, there is no particular limitation on the type of the organic solvent, which thus may be a protonic solvent or an aprotic solvent. The molecular weight of the organic solvent is preferably 20 to 150, particularly preferably 30 to 110. When the molecular weight of the organic solvent is in the range described above, the size of solvated ions becomes smaller, and their diffusivity is enhanced.

Polyvalent metal ions contained in the organic solvent before purification are not particularly limited, and examples thereof include magnesium ions (divalent), chromium ions (divalent, trivalent, or hexavalent), zinc ions (divalent), aluminum ions (trivalent), nickel ions (divalent), manganese ions (divalent to heptavalent), molybdenum ions (divalent to hexavalent), titanium ions (divalent to tetravalent), niobium ions (divalent to tetravalent), and copper ions (divalent). Of these, magnesium ions, chromium ions, and zinc ions are likely to exert an effect of removing polyvalent metal ions of the present invention. Note that the content of the polyvalent metal ions in the organic solvent before purification depends on the usage of the organic solvent.

The monolithic organic porous ion exchanger according to the method for purifying an organic solvent of the present invention is a monolithic organic porous body into which either cation exchange groups or anion exchange groups have been introduced. The monolithic organic porous body according to the monolithic organic porous ion exchanger is a porous body including a skeleton formed by an organic polymer and having a large number of communicating holes, as flow passages for reaction liquid, defined by the skeleton. The monolithic organic porous ion exchanger is a porous body in which either cation exchange groups or anion exchange groups have been introduced so as to uniformly distribute in the skeleton of the monolithic organic porous body. Note that, herein, the "monolithic organic porous body" is simply referred to as the "monolith" and the "monolithic organic porous ion exchanger" is simply referred to as the "monolith ion exchanger". Additionally, a "monolithic organic porous intermediate" as an intermediate (a precursor of a second monolith or third monolith) in production of the second monolith or third monolith is also simply referred to as a "monolith intermediate".

The monolith ion exchanger according to the method for purifying an organic solvent of the present invention, which is obtained by introducing either cation exchange groups or anion exchange groups into a monolith, is an organic porous body comprising a continuous skeleton phase and a continuous hole phase in its structure. The thickness of the continuous skeleton is 1 to 100 µm, the average diameter of continuous holes is 1 to 1000 µm, and the total pore volume is 0.5 to 50 mL/g.

The thickness of the continuous skeleton of the monolith ion exchanger in a dry state is 1 to 100 µm. A thickness of the continuous skeleton of the monolith ion exchanger of less than 1 µm is not preferable because, besides a disadvantage of a decrease in the ion exchange capacity per volume, the mechanical strength decreases, causing a considerable deformation of the monolith ion exchanger especially upon liquid passage at a high flow rate. Furthermore, a thickness of less than 1 µm is not preferable because the contact efficiency between the organic solvent and the monolith ion exchanger is reduced, and thus the efficiency of removing polyvalent metal ions is reduced. In contrast, a thickness of the continuous skeleton of the monolith ion exchanger exceeding 100 µm is not preferable because the skeleton becomes extremely thick and it takes a longer time for metal ions to diffuse. The thickness of the continuous skeleton is determined by SEM observation.

The average diameter of the continuous holes of the monolith ion exchanger in a dry state is 1 to 1000 µm. An average diameter of the continuous holes of the monolith ion exchanger of less than 1 µm is not preferable because the pressure loss upon liquid passage increases. In contrast, an average diameter of the continuous holes of the monolith ion exchanger exceeding 1000 µm is not preferable because the organic solvent insufficiently contacts the monolith ion exchanger, and thus the efficiency of removing polyvalent metal ions is reduced. Note that the average diameter of the continuous holes of the monolith ion exchanger in a dry state is measured by mercury porosimetry and indicates the maximal value of a pore distribution curve obtained by mercury porosimetry.

The total pore volume of the monolith ion exchanger in a dry state is 0.5 to 50 mL/g. A total pore volume of the monolith ion exchanger of less than 0.5 mL/g is not preferable because the pressure loss upon liquid passage increases, and furthermore, because the amount of a liquid that permeates per unit cross-sectional area is reduced, and thus the throughput is reduced. In contrast, a total pore volume of the monolith ion exchanger exceeding 50 mL/g is not preferable because the ion exchange capacity per volume is reduced, and thus the efficiency of removing polyvalent metal ions is reduced. Moreover, a total pore volume exceeding 50 mL/g is not preferable because the mechanical strength decreases, causing a considerable deformation of the monolith ion exchanger especially upon liquid passage at a high flow rate, and the pressure loss upon liquid passage abruptly increases. Furthermore, the contact efficiency between the organic solvent and the monolith ion exchanger is reduced, and thus the efficiency of removing polyvalent metal ions is significantly reduced. Note that the total pore volume is measured by mercury porosimetry.

Examples of the structure of such a monolith ion exchanger include open-cell structures disclosed in Japanese Patent Laid-Open Nos. 2002-306976 and 2009-62512, a bicontinuous structure disclosed in Japanese Patent Laid-Open No. 2009-67982, a particle-agglomeration type structure disclosed in Japanese Patent Laid-Open No. 2009-7550, and a composite particle type structure disclosed in Japanese Patent Laid-Open No. 2009-108294.

The ion exchange capacity per weight of the monolith ion exchanger in a dry state is 1 to 6 mg equivalents/g. An ion exchange capacity of the monolith ion exchanger in a dry state of less than 1 mg equivalent/g is not preferable because the throughput of a liquid to be treated is reduced. In contrast, an ion exchange capacity exceeding 6 mg equivalents/g is not preferable because introduction reaction of cation exchange groups is carried out under severe conditions. When the monolith ion exchanger is a monolith anion exchanger, anion exchange groups have been introduced into the monolith anion exchanger, and the anion exchange capacity per weight in a dry state is 1 to 6 mg equivalents/g. When the monolith ion exchanger is a monolith cation exchanger, cation exchange groups have been introduced into the monolith cation exchanger, and the cation exchange capacity per weight in a dry state is 1 to 6 mg equivalents/g. Note that the ion exchange capacity of a porous body including ion exchange groups introduced only on the surface of the skeleton is at most 500 µg equivalents/g, although not determined unconditionally depending on the type of the porous body and ion exchange groups.

The ion exchange groups introduced into the monolith ion exchanger are uniformly distributed not only on the surface of the monolith but also inside the skeleton of the monolith. The expression "ion exchange groups are uniformly distributed" used herein indicates that ion exchange groups are uniformly distributed on the surface and inside the skeleton at least in a µm order. The distribution situation of the ion exchange groups is easily checked by using an EPMA. When the ion exchange groups are uniformly distributed not only on the surface of the monolith but also inside the skeleton of the monolith, the surface and the inside can have uniform physical properties and chemical properties, and thus the resistance to swelling and contraction is improved.

The ion exchange groups introduced into the monolith ion exchanger are either cation exchange groups or anion exchange groups. Examples of the cation exchange group include a carboxylic acid group, an iminodiacetic acid group, a sulfonic acid group, a phosphoric acid group, and a phosphate group. Examples of the anion exchange group include a quaternary ammonium group such as a trimethyl ammonium group, a triethyl ammonium group, a tributyl ammonium group, a dimethyl hydroxyethyl ammonium group, a dimethyl hydroxypropyl ammonium group, and a methyl dihydroxyethyl ammonium group, a tertiary sulfonium group, and a phosphonium group.

A material constituting the continuous skeleton in the monolith ion exchanger is an organic polymer material having a crosslinked structure. The crosslink density of the polymer material is not particularly limited, and the crosslinked structural unit content is 0.1 to 30 mol %, preferably 0.1 to 20 mol % based on all constituent units constituting the polymer material. A crosslinked structural unit content of less than 0.1 mol % is not preferable because the mechanical strength is insufficient. In contrast, a crosslinked structural unit content exceeding 30 mol % is not preferable because introduction of ion exchange groups may become difficult. The types of the polymer material are not particularly limited, and examples thereof include crosslinked polymers such as aromatic vinyl polymers such as polystyrene, poly (α-methylstyrene), polyvinyltoluene, polyvinylbenzyl chloride, polyvinyl biphenyl, and polyvinylnaphthalene; polyolefins such as polyethylene and polypropylene; poly (halogenated polyolefins) such as polyvinyl chloride and polytetrafluoroethylene; nitrile polymers such as polyacrylonitrile; and (meth)acrylic polymers such as polymethyl methacrylate, polyglycidyl methacrylate, and polyethyl acrylate. The above polymers may be polymers obtained by copolymerizing a single type of a vinyl monomer with a crosslinking agent, polymers obtained by polymerizing a plurality of vinyl monomers with a crosslinking agent, or blends of two or more polymers. Of these organic polymer materials, from the viewpoint of ease of formation of a continuous structure, ease of introduction of ion exchange groups, high mechanical strength, and excellent stability in acid or alkali, crosslinked aromatic vinyl polymers are preferable. Examples of particularly preferable materials include styrene-divinylbenzene copolymers and vinylbenzyl chloride-divinylbenzene copolymers.

<Exemplary Embodiment of Monolithic Organic Porous Body and Monolithic Organic Porous Ion Exchanger>

Exemplary embodiments of the monolith include first to third monoliths shown below. Examples of the monolith ion exchanger include first to third monolith ion exchangers shown below.

<Description of First Monolith and First Monolith Ion Exchanger>

A first monolith ion exchanger is a monolith ion exchanger having an open-cell structure in which cellular macropores overlap and the overlapping macropores form openings having an average diameter of 1 to 1000 µm, the first monolith exchanger having a total pore volume of 1 to 50 mL/g, ion exchange groups being uniformly distributed in the organic porous ion exchanger, and an ion exchange capacity per weight in a dry state of 1 to 6 mg equivalents/g. A first monolith, which is a monolith before ion exchange groups are introduced, is an organic porous body having an open-cell structure in which cellular macropores overlap and the overlapping macropores form openings having an average diameter of 1 to 1000 µm, and a total pore volume of 1 to 50 mL/g.

The first monolith ion exchanger includes an open-cell structure (continuous macropore structure) in which cellular macropores overlap and the overlapping macropores form common openings (mesopores) having an average diameter of 1 to 1000 µm, preferably 10 to 200 µm, particularly preferably 20 to 100 µm in a dry state, and most of the mesopores have an open pore structure. In the open pore structure, cells formed from the macropores and the mesopores serve as flow passages for water. An overlap of macropores include 1 to 12 macropores, with many overlaps having 3 to 10 macropores. In FIG. 1, a scanning electron microscope (SEM) photograph of an exemplary embodiment of the first monolith ion exchanger is shown. The first monolith ion exchanger shown in FIG. 1, which has a large number of cellular macropores, includes an open-cell structure in which the cellular macropores overlap and the overlapping macropores form common openings (mesopores), and most of the mesopores have an open pore structure. An average diameter of the mesopores in a dry state of less than 1 µm is not preferable because the pressure loss upon liquid passage significantly increases. An average diameter of mesopores in a dry state exceeding 1000 µm is not preferable because the organic solvent insufficiently contacts the monolith ion exchanger, and thus the efficiency of removing polyvalent metal ions is reduced. When the first monolith ion exchanger takes the open-cell structure as described above, it is possible to form macropore groups and mesopore groups uniformly, and additionally to markedly increase the pore volume and specific surface area, as compared with those of particle-agglomeration type porous bodies described in Japanese Patent Laid-Open No. 8-252579 and the like.

Note that, in the present invention, the average diameter of the openings of the first monolith in a dry state and the average diameter of the openings of the first monolith ion exchanger in a dry state are measured by mercury porosimetry and each indicate the maximal value of a pore distribution curve obtained by mercury porosimetry.

The total pore volume per weight of the first monolith ion exchanger in a dry state is 1 to 50 mL/g, preferably 2 to 30 mL/g. A total pore volume of less than 1 mL/g is not preferable because the pressure loss upon liquid passage increases, and furthermore, because the amount of permeation per unit cross-sectional area is reduced, and thus the treatment capacity is reduced. In contrast, a total pore volume exceeding 50 mL/g is not preferable because the mechanical strength decreases, causing a considerable deformation of the monolith ion exchanger especially upon liquid passage at a high flow rate. Furthermore, a total pore volume exceeding 50 mL/g is not preferable because the contact efficiency between the organic solvent and the monolith ion exchanger is reduced, and thus the efficiency of removing polyvalent metal ions is reduced. The total pore volume of conventional particulate porous ion exchange resins is at most 0.1 to 0.9 mL/g, and then, it is possible to use unconventional exchangers having a higher pore volume of 1 to 50 mL/g and a higher specific surface area than those of conventional ones.

In the first monolith ion exchanger, the material constituting the skeleton is an organic polymer material having a crosslinked structure. The crosslink density of the polymer material is not particularly limited, and the crosslinked structural unit content is 0.3 to 10 mol %, preferably 0.3 to 5 mol % based on all constituent units constituting the polymer material. A crosslinked structural unit content of less than 0.3 mol % is not preferable because the mechanical strength is insufficient. In contrast, a crosslinked structural unit content exceeding 10 mol % is not preferable because introduction of ion exchange groups may become difficult.

The types of the organic polymer material constituting the skeleton of the first monolith ion exchanger are not particularly limited, and examples thereof include crosslinked polymers such as aromatic vinyl polymers such as polystyrene, poly(α-methylstyrene), polyvinyltoluene, polyvinylbenzyl chloride, polyvinyl biphenyl, and polyvinylnaphthalene; polyolefins such as polyethylene and polypropylene; poly(halogenated polyolefins) such as polyvinyl chloride and polytetrafluoroethylene; nitrile polymers such as polyacrylonitrile; and (meth)acrylic polymers such as polymethyl methacrylate, polyglycidyl methacrylate, and polyethyl acrylate. The above organic polymers may be polymers obtained by copolymerizing a single type of a vinyl monomer with a crosslinking agent, polymers obtained by polymerizing a plurality of vinyl monomers with a crosslinking agent, or blends of two or more polymers. Of these organic polymer materials, from the viewpoint of ease of formation of a continuous macropore structure, ease of introduction of ion exchange groups, high mechanical strength, and excellent stability in acid or alkali, crosslinked aromatic vinyl polymers are preferable. Examples of particularly preferable materials include styrene-divinylbenzene copolymers and vinylbenzyl chloride-divinylbenzene copolymers.

The ion exchange groups introduced into the first monolith ion exchanger are the same as in a second monolith ion exchanger and third monolith ion exchanger. The ion exchange groups are cation exchange groups or anion exchange groups. Examples of the cation exchange group include a carboxylic acid group, an iminodiacetic acid group, a sulfonic acid group, a phosphoric acid group, and a phosphate group, and examples of the anion exchange group include a quaternary ammonium group such as a trimethyl ammonium group, a triethyl ammonium group, a tributyl ammonium group, a dimethyl hydroxyethyl ammonium group, a dimethyl hydroxypropyl ammonium group, and a methyl dihydroxyethyl ammonium group, a tertiary sulfonium group, and a phosphonium group.

In the first monolith ion exchanger (also in the second monolith ion exchanger and the third monolith ion exchanger), the ion exchange groups introduced are uniformly distributed not only on the surface of the porous body but also inside the skeleton of the porous body. The expression "ion exchange groups are uniformly distributed" used herein indicates that ion exchange groups are uniformly distributed on the surface and inside the skeleton at least in a µm order. The distribution situation of the ion exchange groups is checked by using an EPMA. When the ion exchange groups are uniformly distributed not only on the surface of the monolith but also inside the skeleton of the porous body, the surface and the inside can have uniform physical properties and chemical properties, and thus the resistance to swelling and contraction is improved.

The ion exchange capacity per weight of the first monolith ion exchanger in a dry state is 1 to 6 mg equivalents/g. When the ion exchange capacity per weight in a dry state is in the range described above, the efficiency of removing polyvalent metal ions is improved. When the first monolith ion exchanger is a monolith anion exchanger, anion exchange groups have been introduced into the first monolith anion exchanger, and the anion exchange capacity per weight in a dry state is 1 to 6 mg equivalents/g. When the first monolith ion exchanger is a monolith cation exchanger, cation exchange groups have been introduced into the first monolith cation exchanger, and the cation exchange capacity per weight in a dry state is 1 to 6 mg equivalents/g.

<Method for Producing First Monolith and First Monolith Ion Exchanger>

A method for producing the first monolith is not particularly limited, and an exemplary production method in accordance with the method described in Japanese Patent Laid-Open No. 2002-306976 is shown below. That is, the first monolith is obtained by mixing oil-soluble monomers including no ion exchange group, a surfactant, water, and a polymerization initiator as required to form a water-in-oil emulsion and polymerizing the water-in-oil emulsion to form a monolith. Such a method for producing the first monolith is preferable in that the porous structure of the monolith is easily controlled.

Examples of the oil-soluble monomer including no ion exchange group used for production of the first monolith include lipophilic monomers that do not include any of ion exchange groups such as a carboxylic acid group and a sulfonic acid group and anion exchange groups such as a quaternary ammonium group and have low solubility in water. Specific examples of these monomers include styrene, α-methylstyrene, vinyltoluene, vinylbenzyl chloride, divinylbenzene, ethylene, propylene, isobutene, butadiene, isoprene, chloroprene, vinyl chloride, vinyl bromide, vinylidene chloride, tetrafluoroethylene, acrylonitrile, methacrylonitrile, vinyl acetate, methyl acrylate, ethyl acrylate, butyl acrylate, 2-ethylhexyl acrylate, trimethylolpropane triacrylate, butanediol diacrylate, methyl methacrylate, ethyl methacrylate, propyl methacrylate, butyl methacrylate, 2-ethylhexyl methacrylate, cyclohexyl methacrylate, benzyl methacrylate, glycidyl methacrylate, and ethylene glycol dimethacrylate. These monomers may be used either singly or in combinations of two or more. In the present invention, note that it is preferable to select a crosslinkable monomer, such as divinylbenzene or ethylene glycol dimethacrylate, as at least one component of the oil-soluble monomers and set the crosslinkable monomer content to 0.3 to 10 mol %, preferably 0.3 to 5 mol % based on the total oil-soluble monomers, in that ion exchange groups can be quantitatively introduced in a later step and a practically sufficient mechanical strength can be achieved.

The surfactant used for production of the first monolith is not particularly limited provided that a water-in-oil (W/O) emulsion can be formed by mixing the oil-soluble monomers including no ion exchange group with water. Examples of the surfactant that can be used include nonionic surfactants such as sorbitan monooleate, sorbitan monolaurate, sorbitan monopalmitate, sorbitan monostearate, sorbitan trioleate, polyoxyethylene nonyl phenyl ether, polyoxyethylene stearyl ether, and polyoxyethylene sorbitan monooleate; anionic surfactants such as potassium oleate, sodium dodecylbenzenesulfonate, and sodium dioctyl sulfosuccinate; cationic surfactants such as distearyl dimethylammonium chloride; and amphoteric surfactants such as lauryldimethyl betaine. These surfactants may be used either singly or in combinations of two or more. The term "water-in-oil emulsion" refers to an emulsion in which water droplets are dispersed in a continuous oil phase. The amount of the surfactant added depends on the type of the oil-soluble monomer and the size of the emulsion particles (macropores) intended, but, although not always the case, can be normally selected within the range of about 2 to 70% based on the total amount of the oil-soluble monomer and the surfactant. In order to control the shape and size of cells in the monolith, an alcohol, such as methanol and stearyl alcohol; a carboxylic acid, such as stearic acid; a hydrocarbon, such as octane, dodecane, and toluene; and a cyclic ether, such as tetrahydrofuran and dioxane can also coexist in the system, although it is not necessarily essential.

In production of the first monolith, as a polymerization initiator, which is used as required when the monolith is formed by polymerization, a compound that generates radicals by heat and light irradiation is suitably used. The polymerization initiator may be water-soluble or oil-soluble, and examples thereof include azobisisobutyronitrile, azobisdimethylvaleronitrile, azobiscyclohexanenitrile, azobiscyclohexanecarbonitrile, benzoyl peroxide, potassium persulfate, ammonium persulfate, hydrogen peroxide-ferrous chloride, sodium persulfate-sodium hydrogen sulfite, and tetramethylthiuram disulfide. However, polymerization may proceed only by heating or light irradiation without addition of a polymerization initiator in some systems. Thus, it is not necessary to add a polymerization initiator to such systems.

In production of the first monolith, a mixing method in which oil-soluble monomers including no ion exchange group, a surfactant, water, and a polymerization initiator are mixed to form a water-in-oil emulsion is not particularly limited. It is possible to use a method in which the components may be mixed all together, a method in which oil-soluble components including the oil-soluble monomers, surfactant, and oil-soluble polymerization initiator and water-soluble components including water and the water-soluble polymerization initiator are each uniformly dissolved separately, and then, both the components are mixed, or the like. Mixing apparatuses for forming the emulsion are also not particularly limited. A common mixer, homogenizer, high-pressure homogenizer, so-called planetary stirrer for stirring and mixing a material to be treated placed into a mixing vessel, which is held inclined and caused to move around a revolution axis while rotating, or the like may be used. Any apparatus suitable for achieving a target particle size of the emulsion may be selected. The mixing conditions are also not particularly limited, and it is possible to set any stirring speed and stirring time for achieving a target particle size of the emulsion. Of these mixing apparatuses, a planetary stirrer, which enables water droplets in a W/O emulsion to uniformly generate and can set the average diameter of the droplets to any value within a wide range, is preferably used.

In production of the first monolith, various conditions for polymerizing the water-in-oil emulsion thus obtained can be selected depending on the type of monomers and the initiator system. For example, when azobisisobutyronitrile, benzoyl peroxide, potassium persulfate, or the like is used as the polymerization initiator, the emulsion may be polymerized with heating at 30 to 100° C. for 1 to 48 hours in a sealed vessel in an inert atmosphere. When hydrogen peroxide-ferrous chloride, sodium persulfate-sodium hydrogen sulfite, or the like is used as the initiator, the emulsion may be polymerized with heating at 0 to 30° C. for 1 to 48 hours in a sealed vessel under an inert atmosphere. After polymerization, the content is removed and Soxhlet-extracted with a solvent such as isopropanol to remove the unreacted monomers and the remaining surfactant, thereby obtaining the first monolith.

A method for producing the first monolith ion exchanger is not particularly limited. Examples thereof include a method in which monomers containing an ion exchange group, for example, monomers prepared by introducing an ion exchange group such as a carboxylic acid group and a sulfonic acid group into the above oil-soluble monomers including no ion exchange groups, are polymerized instead of monomers including no ion exchange group in the above method for producing the first monolith, so as to produce a monolith ion exchanger in one stage, and a method in which monomers including no ion exchange groups are polymerized to form a first monolith and then, ion exchange groups are introduced thereinto. Of these methods, the method in which monomers including no ion exchange groups are polymerized to form a first monolith and then, ion exchange groups are introduced thereinto is preferable because the porous structure of the monolith ion exchanger is easily controlled and ion exchange groups can be quantitatively introduced.

The method for introducing ion exchange groups into the first monolith is not particularly limited, and a known method such as a polymer reaction or graft polymerization may be used. Examples of a method for introducing quaternary ammonium groups, when the monolith is a styrene-divinylbenzene copolymer or the like, include a method in which chloromethyl groups are introduced using chloromethyl methyl ether or the like and then the monolith is allowed to react with tertiary amine; a method in which monolith is produced by copolymerizing chloromethylstyrene and divinylbenzene and allowed to react with tertiary amine; a method in which radical initiator groups or chain transfer groups are introduced into the monolith and N,N,N-trimethylammoniumethyl acrylate or N,N,N-trimethylammoniumpropyl acrylamide is graft-polymerized thereon; and a method in which glycidyl methacrylate is graft-polymerized in the same manner and then quaternary ammonium groups are introduced by functional group transformation. Of these methods, as the method for introducing quaternary ammonium groups, the method in which chloromethyl groups are introduced into a styrene-divinylbenzene copolymer using chloromethyl methyl ether or the like and then the copolymer is allowed to react with tertiary amine and the method in which monolith is produced by copolymerizing chloromethylstyrene and divinylbenzene and allowed to react with tertiary amine are preferable in that ion exchange groups can be introduced uniformly and quantitatively. Note that examples of the anion exchange group to be introduced include a quaternary ammonium group, such as a trimethyl ammonium group, a triethyl ammonium group, a tributyl ammonium group, a dimethyl hydroxyethyl ammonium group, a dimethyl hydroxypropyl ammonium group, and a methyl dihydroxyethyl ammonium group, a tertiary sulfonium group, and a phosphonium group. Examples of a method for introducing sulfonic acid groups, when the monolith is a styrene-divinylbenzene copolymer or the like, include a method in which the monolith is sulfonated using chlorosulfuric acid, concentrated sulfuric acid, or fuming sulfuric acid; a method in which radical initiator groups or chain transfer groups are uniformly introduced onto the surface of the skeleton or inside the skeleton of the monolith, and sodium styrenesulfonate or acrylamide-2-methylpropanesulfonic acid is graft-polymerized thereon; and a method in which glycidyl methacrylate is graft-polymerized in the same manner and then sulfonic acid groups are introduced by functional group transformation. Of these methods, the method in which sulfonic acid is introduced into a styrene-divinylbenzene copolymer using chlorosulfuric acid is preferable in that ion exchange groups can be introduced uniformly and quantitatively. Note that examples of the cation exchange group to be introduced include a cationic exchange group such as a carboxylic acid group, an iminodiacetic acid group, a sulfonic acid group, a phosphoric acid group, and a phosphate group.

<Description of Second Monolith and Second Monolith Ion Exchanger>

A second monolith ion exchanger includes a continuous macropore structure in which cellular macropores overlap and the overlapping macropores form openings having an average diameter of 30 to 300 µm in a dry state, the monolith ion exchanger having a total pore volume of 0.5 to 10 mL/g in a dry state, an area of the skeleton portion appearing in cross section being 25 to 50% based on the image area in a SEM image of a cut section of the continuous macropore structure (dry body), and an ion exchange capacity per weight in a dry state of 1 to 6 mg equivalents/g, and the ion exchange groups being uniformly distributed in the organic porous ion exchanger. The second monolith, which is a monolith before ion exchange groups are introduced, is an organic porous body including a continuous macropore structure in which cellular macropores overlap and the overlapping macropores form openings having an average diameter of 30 to 300 µm in a dry state, the monolith having a total pore volume in a dry state of 0.5 to 10 mL/g and an area of the skeleton portion appearing in cross section in a SEM image of a cut section of the continuous macropore structure (dry body) being 25 to 50% based on the image area.

Figure 2:
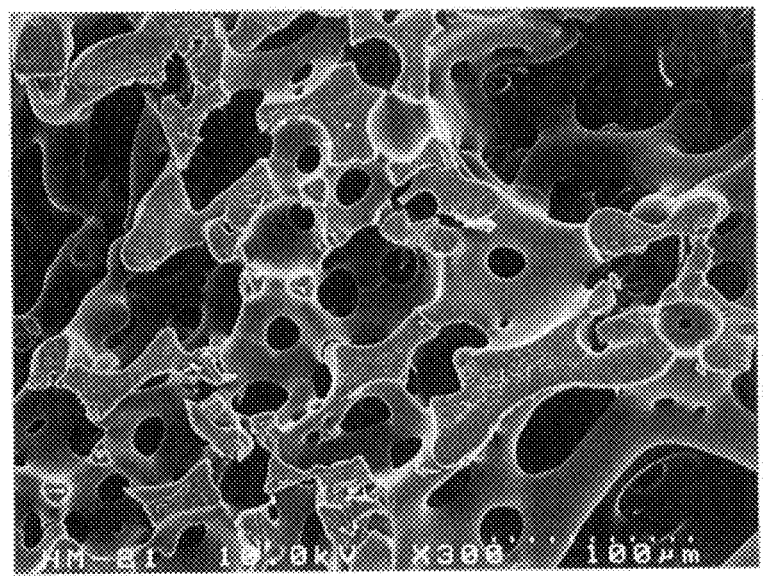
FIG. 2 is a SEM photograph of an exemplary embodiment of a second monolithic organic porous cation exchanger.

The second monolith ion exchanger includes a continuous macropore structure in which cellular macropores overlap and the overlapping macropores form openings (mesopores) in a dry state having an average diameter of 30 to 300 µm, preferably 30 to 200 µm, particularly preferably 40 to 100 µm. In FIG. 2, a SEM photograph of an exemplary embodiment of the second monolith ion exchanger is shown. The second monolith ion exchanger shown in FIG. 2, which has a large number of cellular macropores, includes a continuous macropore structure in which the cellular macropores overlap and the overlapping macropores form common openings (mesopores), and most of the mesopores have an open pore structure. An average diameter of the openings in a dry state of less than 30 µm is not preferable because the pressure loss upon liquid passage increases. An excessively large average diameter of the openings in a dry state is not preferable because the organic solvent insufficiently contacts the monolith ion exchanger and, as a result, the efficiency of removing polyvalent metal ions is reduced.

Note that the average diameter of the openings of the second monolith in a dry state, the average diameter of the openings of the second monolith ion exchanger in a dry state, and the average diameter of the openings of a second monolith intermediate (2) in a dry state to be obtained in the step I of production of second monolith described below are measured by mercury porosimetry and each indicate the maximal value of a pore distribution curve obtained by mercury porosimetry.

In the second monolith ion exchanger, in the SEM image of a cut section of the open-cell structure (continuous macropore structure) (dry body), an area of the skeleton portion appearing in cross section is 25 to 50%, preferably 25 to 45% based on the image area. An area of the skeleton portion appearing in cross section of less than 25% based on the image area is not preferable because the skeleton becomes thinner, and the mechanical strength decreases, causing a considerable deformation of the monolith ion exchanger especially upon liquid passage at a high flow rate. Furthermore, an area of the skeleton portion of less than 25% based on the image area is not preferable because the contact efficiency between the organic solvent and the monolith ion exchanger is reduced, and thus the efficiency of removing polyvalent metal ions is reduced. In contrast, an area of the skeleton portion exceeding 50% is not preferable because the skeleton becomes excessively thick, and thus the pressure loss upon liquid passage increases.

Figure 3:
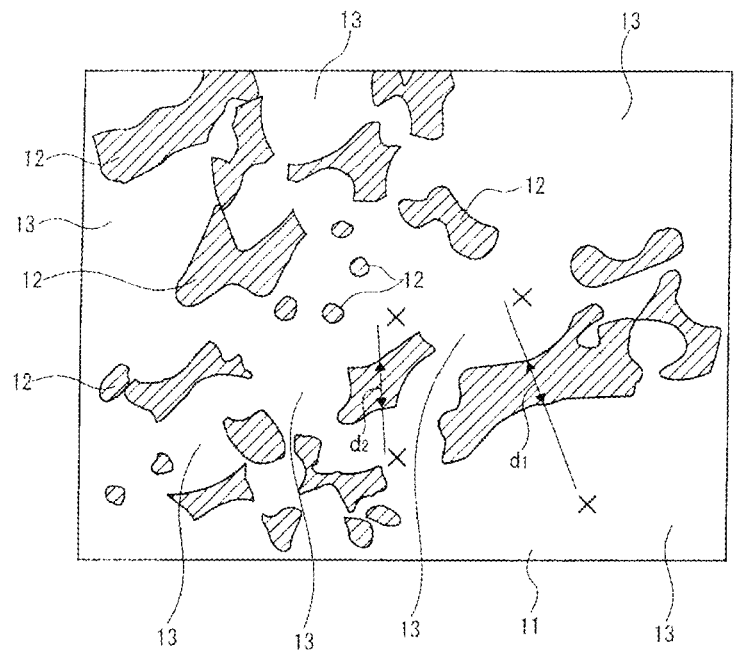
FIG. 3 is a transcription of a skeleton portion appearing as cross section in the SEM photograph of FIG. 2.

Conditions for obtaining the SEM image are only required to be conditions under which the skeleton portion appearing in cross section in the cut section is clearly observed. For example, the magnification is 100 to 600, and the photographic area is about 150 mm×100 mm. SEM observation is preferably conducted on three or more images, preferably five or more images, of different cut points and photographing points, photographed at optional points in any cut section of the second monolith ion exchanger without subjectivity. The second monolith ion exchanger to be cut, which is subjected to electron microscopy, is in a dry state. A skeleton portion in the cut section in the SEM image is described with reference to FIGS. 2 and 3. FIG. 3 is a transcription of a skeleton portion appearing as cross section in the SEM photograph of FIG. 2. In FIGS. 2 and 3, portions having a generally irregular shape and appearing in cross section are "skeleton portions appearing in cross section (reference sign 12)". Circular holes appearing in FIG. 2 are openings (mesopores), and portions having a relatively large curvature or a relatively large curved surface are macropores (reference sign 13 in FIG. 3). The area of the skeleton portions appearing in cross section in FIG. 3 accounts for 28% of the rectangular image area 11. The skeleton portions can thus be clearly identified.

A method for measuring the area of the skeleton portions appearing in cross section in the cut section in the SEM image is not particularly limited. Examples of the method include a method in which the skeleton portions is identified by known computer processing or the like and then the area of the skeleton portions is calculated automatically using a computer or the like or manually. Examples of the manual calculation method include a method in which an area having an irregular shape is substituted with an aggregate such as a quadrangle, a triangle, a circle, and a trapezoid and such areas are laminated to determine the total area.

The total pore volume per weight of the second monolith ion exchanger in a dry state is 0.5 to 10 mL/g, preferably 0.8 to 8 mL/g. A total pore volume of less than 0.5 mL/g is not preferable because the pressure loss upon liquid passage increases, and furthermore, because the amount of fluid permeated per unit cross-sectional area is reduced, and thus the treatment capacity decreases. In contrast, a total pore volume exceeding 10 mL/g is not preferable because the mechanical strength decreases, causing a considerable deformation of the monolith ion exchanger especially upon liquid passage at a high flow rate. Furthermore, a total pore volume exceeding 10 mL/g is not preferable because the contact efficiency between the organic solvent and the monolith ion exchanger is reduced, and thus the efficiency of removing polyvalent metal ions is reduced.

In the second monolith ion exchanger, the material constituting the skeleton is an organic polymer material having a crosslinked structure. The crosslink density of the polymer material is not particularly limited, and the crosslinked structural unit content is 0.3 to 10 mol %, preferably 0.3 to 5 mol % based on all constituent units constituting the polymer material. A crosslinked structural unit content of less than 0.3 mol % is not preferable because the mechanical strength is insufficient. In contrast, a crosslinked structural unit content exceeding 10 mol % is not preferable because introduction of ion exchange groups may become difficult.

The types of the polymer material constituting the skeleton of the second monolith ion exchanger are not particularly limited, and examples thereof include crosslinked polymers such as aromatic vinyl polymers such as polystyrene, poly(α-methylstyrene), polyvinyltoluene, polyvinylbenzyl chloride, polyvinyl biphenyl, and polyvinylnaphthalene; polyolefins such as polyethylene and polypropylene; poly(halogenated polyolefins) such as polyvinyl chloride and polytetrafluoroethylene; nitrile polymers such as polyacrylonitrile; and (meth)acrylic polymers such as polymethyl methacrylate, polyglycidyl methacrylate, and polyethyl acrylate. The above polymers may be polymers obtained by copolymerizing a single type of a vinyl monomer with a crosslinking agent, polymers obtained by polymerizing a plurality of vinyl monomers with a crosslinking agent, or blends of two or more polymers. Of these organic polymer materials, from the viewpoint of ease of formation of a continuous macropore structure, ease of introduction of ion exchange groups, high mechanical strength if ion exchange groups are introduced, and excellent stability in acid or alkali, crosslinked aromatic vinyl polymers are preferable. Examples of particularly preferable materials include styrene-divinylbenzene copolymers and vinylbenzyl chloride-divinylbenzene copolymers.

The ion exchange groups introduced into the second monolith ion exchanger are the same as the ion exchange groups introduced into the first monolith ion exchanger.

The ion exchange groups introduced into the second monolith ion exchanger are uniformly distributed not only on the surface of the porous body but also inside the skeleton of the porous body.

The ion exchange capacity per weight of the second monolith ion exchanger in a dry state is 1 to 6 mg equivalents/g. In the second monolith ion exchanger, the diameter of the openings can be further increased as well as the skeleton of the continuous macropore structure can be thickened (the wall section of the skeleton is thickened), and thus the ion exchange capacity per volume can be dramatically increased while the pressure loss is suppressed low. When the ion exchange capacity per weight in a dry state is in the range described above, the efficiency of removing polyvalent metal ions is improved. When the second monolith ion exchanger is a monolith anion exchanger, anion exchange groups have been introduced into the second monolith anion exchanger, and the anion exchange capacity per weight in a dry state is 1 to 6 mg equivalents/g. When the second monolith ion exchanger is a monolith cation exchanger, cation exchange groups have been introduced into the second monolith cation exchanger, and the cation exchange capacity per weight in a dry state is 1 to 6 mg equivalents/g.

<Method for Producing Second Monolith and Second Monolith Ion Exchanger>

The second monolith can be obtained by performing a step I of stirring a mixture of oil-soluble monomers including no ion exchange group, a surfactant, and water to prepare a water-in-oil emulsion and then polymerizing the water-in-oil emulsion to obtain a monolithic organic porous intermediate (hereinbelow, also referred to as the monolith intermediate (2)) including a continuous macropore structure having a total pore volume of 5 to 16 mL/g, a step II of preparing a mixture of vinyl monomers, a crosslinking agent having at least two or more vinyl groups in one molecule, an organic solvent that dissolves the vinyl monomers and crosslinking agent but does not dissolve a polymer produced by polymerizing the vinyl monomers, and a polymerization initiator, and a step III of polymerizing the mixture obtained in the step II in a stationary state and in the presence of the monolith intermediate (2) obtained in the step I to obtain a second monolith having a skeleton thicker than that of the monolith intermediate (2).

In the method for producing the second monolith, the step I is only required to be carried out in compliance with the method described in Japanese Patent Laid-Open No. 2002-306976.

In production of the monolith intermediate (2) of the step I according to the method for producing the second monolith, examples of the oil-soluble monomer including no ion exchange group include monomers that include no ion exchange group such as a carboxylic acid group, a sulfonic acid group, and a quaternary ammonium group, have low solubility in water, and is lipophilic. Suitable examples of these monomers include styrene, α-methylstyrene, vinyltoluene, vinylbenzyl chloride, divinylbenzene, ethylene, propylene, isobutene, butadiene, and ethylene glycol dimethacrylate. These monomers may be used either singly or in combinations of two or more. Note that it is preferable to select a crosslinkable monomer, such as divinylbenzene or ethylene glycol dimethacrylate, as at least one component of oil-soluble monomers and set the content of the crosslinkable monomer to 0.3 to 10 mol %, preferably 0.3 to 5 mol % based on the total oil-soluble monomers because the amount of ion exchange groups, if introduced, can be quantitatively introduced.

The surfactant used in the step I according to the method for producing the second monolith is not particularly limited provided that a water-in-oil (W/O) emulsion can be formed by mixing the oil-soluble monomers including no ion exchange group with water. Examples of the surfactant that can be used include nonionic surfactants such as sorbitan monooleate, sorbitan monolaurate, sorbitan monopalmitate, sorbitan monostearate, sorbitan trioleate, polyoxyethylene nonyl phenyl ether, polyoxyethylene stearyl ether, and polyoxyethylene sorbitan monooleate; anionic surfactants such as potassium oleate, sodium dodecylbenzenesulfonate, and sodium dioctyl sulfosuccinate; cationic surfactants such as distearyl dimethylammonium chloride; and amphoteric surfactants such as lauryldimethyl betaine. These surfactants may be used either singly or in combinations of two or more. The term "water-in-oil emulsion" refers to an emulsion in which water droplets are dispersed in a continuous oil phase. The amount of the surfactant added depends on the type of the oil-soluble monomer and the size of the emulsion particles (macropores) intended, but, although not always the case, can be normally selected within the range of about 2 to 70% based on the total amount of the oil-soluble monomer and the surfactant.

In the step I according to the method for producing the second monolith, a polymerization initiator may be used as required when a water-in-oil emulsion is formed. As the polymerization initiator, a compound that generates radicals by heat and light irradiation is suitably used. The polymerization initiator may be water-soluble or oil-soluble, and examples thereof include azobisisobutyronitrile, azobisdimethylvaleronitrile, azobiscyclohexanenitrile, azobiscyclohexanecarbonitrile, benzoyl peroxide, potassium persulfate, ammonium persulfate, hydrogen peroxide-ferrous chloride, sodium persulfate-sodium hydrogen sulfite, and tetramethylthiuram disulfide.

In the step I according to the method for producing the second monolith, a mixing method in which oil-soluble monomers including no ion exchange group, a surfactant, water, and a polymerization initiator are mixed to form a water-in-oil emulsion is not particularly limited. It is possible to use a method in which the components may be mixed all together, a method in which oil-soluble components including the oil-soluble monomers, surfactant, and oil-soluble polymerization initiator and water-soluble components including water and the water-soluble polymerization initiator are each uniformly dissolved separately, and then, both the components are mixed, or the like. Mixing apparatuses for forming the emulsion are also not particularly limited. A common mixer, homogenizer, high-pressure homogenizer, or the like can be used. Any apparatus suitable for achieving a target particle size of the emulsion may be selected. The mixing conditions are also not particularly limited, and it is possible to set any stirring speed and stirring time for achieving a target particle size of the emulsion.

The monolith intermediate (2) obtained in the step I according to the method for producing the second monolith has a continuous macropore structure. When this structure is allowed to coexist in the polymerization system, a porous structure having a thick skeleton is formed based on the structure of the monolith intermediate (2) as a mold. The monolith intermediate (2) is an organic polymer material having a crosslinked structure. The crosslink density of the polymer material is not particularly limited, and the crosslinked structural unit content is 0.3 to 10 mol %, preferably 0.3 to 5 mol % based on all constituent units constituting the polymer material. A crosslinked structural unit content of less than 0.3 mol % is not preferable because the mechanical strength is insufficient. Particularly, with a large total pore volume of 10 to 16 mL/g, the monolith intermediate (2) preferably contains 2 mol % or more of the crosslinked structural unit to maintain the continuous macropore structure. In contrast, a crosslinked structural unit content exceeding 10 mol % is not preferable because introduction of ion exchange groups may become difficult.

In the step I according to the method for producing the second monolith, types of the polymer material for the monolith intermediate (2) are not particularly limited, and examples thereof include the same as the polymer materials for the aforementioned first monolith. This polymer material is used to form a similar polymer for the skeleton of the monolith intermediate (2) in order to thicken the skeleton to thereby obtain the second monolith having a uniform skeleton structure.

The monolith intermediate (2) obtained in the step I according to the method for producing the second monolith has a total pore volume per weight in a dry state of 5 to 16 mL/g, preferably 6 to 16 mL/g. An excessively small total pore volume is not preferable because the total pore volume of the monolith obtained after polymerization of the vinyl monomers is excessively reduced, and thus the pressure loss upon fluid permeation increases. In contrast, an excessively large total pore volume is not preferable because the structure of the monolith obtained after polymerization of the vinyl monomers deviates from the continuous macropore structure. In order to bring the total pore volume of the monolith intermediate (2) to the above numerical range, the ratio between the monomers and water should be set to approximately 1:5 to 1:20.

The monolith intermediate (2) obtained in the step I according to the method for producing the second monolith has an average diameter of the openings (mesopores), which are overlapping macropores, of 20 to 200 μm in a dry state. An average diameter of the openings in a dry state of less than 20 μm is not preferable because the diameter of the openings of the monolith obtained after polymerization of the vinyl monomers becomes smaller, and thus the pressure loss upon liquid passage increases. In contrast, an average diameter exceeding 200 μm is not preferable because the diameter of the openings of the monolith obtained after polymerization of the vinyl monomers excessively enlarges, and thus the reaction liquid insufficiently contacts the monolith anion exchanger and, as a result, the catalyst activity is reduced. It is preferable that the monolith intermediate (2) has a uniform structure in which the macropores have a uniform size and the openings have a uniform diameter. Without limitation thereto, some non-uniform macropores that are larger than the uniform macropores may be interspersed in the uniform structure.

The step II according to the method for producing the second monolith is a step of preparing a mixture of vinyl monomers, a crosslinking agent having at least two vinyl groups in one molecule, an organic solvent that dissolves the vinyl monomers and crosslinking agent but does not dissolve a polymer produced by polymerizing the vinyl monomers, and a polymerization initiator. Note that the steps I and II may be performed in any order and the step II may be performed before or after the step I.

The vinyl monomer used in the step II according to the method for producing the second monolith is not particularly limited provided that the vinyl monomer is a lipophilic vinyl monomer that includes a polymerizable vinyl group in the molecule and has high solubility in an organic solvent. It is preferable to select vinyl monomers used to produce a polymer material that is the same as or similar to the monolith intermediate (2) allowed to coexist in the above polymerization system. Specific examples of these vinyl monomers include aromatic vinyl monomers such as styrene, α-methylstyrene, vinyltoluene, vinylbenzyl chloride, vinylbiphenyl, and vinylnaphthalene; α-olefins such as ethylene, propylene, 1-butene, and isobutene; diene monomers such as butadiene, isoprene, and chloroprene; halogenated olefins such as vinyl chloride, vinyl bromide, vinylidene chloride, and tetrafluoroethylene; nitrile monomers such as acrylonitrile and methacrylonitrile; vinyl esters such as vinyl acetate and vinyl propionate; and (meth)acrylic monomers such as methyl acrylate, ethyl acrylate, butyl acrylate, 2-ethylhexyl acrylate, methyl methacrylate, ethyl methacrylate, propyl methacrylate, butyl methacrylate, 2-ethylhexyl methacrylate, cyclohexyl methacrylate, benzyl methacrylate, and glycidyl methacrylate. These monomers may be used either singly or in combinations of two or more. Vinyl monomers suitably used are aromatic vinyl monomers such as styrene and vinylbenzyl chloride.

The amount of the vinyl monomer added used in the step II according to the method for producing the second monolith is 3 to 50 times by weight, preferably 4 to 40 times by weight the amount of the monolith intermediate (2) allowed to coexist upon polymerization. An amount of the vinyl monomer added of less than 3 times the amount of the monolith intermediate is not preferable because it is not possible to thicken the skeleton of the monolith produced (the wall section of the monolith skeleton) and moreover, if ion exchange groups are introduced, the ion exchange capacity per volume after introduction is reduced. In contrast, an amount of the vinyl monomer added exceeding 50 times is not preferable because the diameter of the openings becomes smaller and the pressure loss upon liquid passage increases.

The crosslinking agent suitably used in the step II according to the method for producing the second monolith includes at least two polymerizable vinyl groups in the molecule and has high solubility in an organic solvent. Specific examples of the crosslinking agent include divinylbenzene, divinylnaphthalene, divinylbiphenyl, ethylene glycol dimethacrylate, trimethylolpropane triacrylate, and butanediol diacrylate. These crosslinking agents may be used either singly or in combinations of two or more. A preferable crosslinking agent is an aromatic polyvinyl compound such as divinylbenzene, divinylnaphthalene, and divinylbiphenyl in respect of high mechanical strength and stability in hydrolysis. It is preferable that the amount of the crosslinking agent used be 0.3 to 10 mol %, particularly 0.3 to 5 mol % based on the total amount of the vinyl monomer and the crosslinking agent. An amount of the crosslinking agent used of less than 0.3 mol % is not preferable because the mechanical strength of the monolith is insufficient. In contrast, an amount exceeding 10 mol % is not preferable because the amount of the ion exchange groups introduced may be reduced. The crosslinking agent is preferably used in an amount so as to achieve a crosslink density substantially equivalent to the crosslink density of the monolith intermediate (2) to coexist upon polymerization of the vinyl monomers/crosslinking agent. If both the amounts used significantly differ from each other, the crosslink density may be unevenly distributed in the monolith produced and cracking of the monolith is likely to occur upon introduction reaction of ion exchange groups.

The organic solvent used in the step II according to the method for producing the second monolith is an organic solvent that dissolves the vinyl monomers and crosslinking agent but does not dissolve a polymer produced by polymerizing the vinyl monomers, that is, a poor solvent for a polymer produced by polymerizing the vinyl monomers. The organic solvent significantly depends on the type of the vinyl monomer, and thus it is difficult to give common specific examples. Examples of the organic solvent used when the vinyl monomer is styrene include alcohols such as methanol, ethanol, propanol, butanol, hexanol, cyclohexanol, octanol, 2-ethylhexanol, decanol, dodecanol, ethylene glycol, propylene glycol, tetramethylene glycol, and glycerol; chain (poly)ethers such as diethyl ether, ethylene glycol dimethyl ether, cellosolve, methyl cellosolve, butyl cellosolve, polyethylene glycol, polypropylene glycol, and polytetramethylene glycol; chain saturated hydrocarbons such as hexane, heptane, octane, isooctane, decane, and dodecane; and esters such as ethyl acetate, isopropyl acetate, cellosolve acetate, and ethyl propionate. Even a good solvent for polystyrene such as dioxane, THF, and toluene may also be used as the organic solvent if the good solvent is used in a small amount together with the poor solvent described above. The organic solvent is preferably used in an amount such that the concentration of the above vinyl monomer is 30 to 80% by weight. A case in which the amount of the organic solvent used deviates from the above range to decrease the concentration of the vinyl monomer to less than 30% by weight is not preferable because the polymerization rate may be reduced or a monolith structure after polymerization may deviates from the range of the third monolith. In contrast, a concentration of the vinyl monomer exceeding 80% by weight is not preferable because polymerization may run away.

As the polymerization initiator used in the step II according to the method for producing the second monolith, a compound that generates radicals by heat or light irradiation is suitably used. The polymerization initiator is preferably oil-soluble. Specific examples of the polymerization initiator include 2,2'-azobis(isobutylonitrile), 2,2'-azobis(2,4-dimethylvaleronitrile), 2,2'-azobis(2-methylbutyronitrile), 2,2'-azobis(4-methoxy-2,4-dimethylvaleronitrile), dimethyl 2,2'-azobisisobutyrate, 4,4'-azobis(4-cyanovaleric acid), 1,1'-azobis(cyclohexane-1-carbonitrile), benzoyl peroxide, lauroyl peroxide, potassium persulfate, ammonium persulfate, and tetramethylthiuram disulfide. The amount of the polymerization initiator used significantly depends on the type of the monomer, the polymerization temperature, and the like. The initiator may be used in an amount in the range of about 0.01 to 5% based on the total amount of the vinyl monomer and the crosslinking agent.

The step III according to the method for producing the second monolith is a step of polymerizing the mixture obtained in the step II in a stationary state and in the presence of the monolith intermediate (2) obtained in the step I to obtain a second monolith having a skeleton thicker than that of the monolith intermediate (2). The monolith intermediate (2) used in the step III serves an extremely important role in creating the second monolith. Allowing the monolith intermediate (2) having the continuous macropore structure to exist in the above polymerization system can provide the second monolith.

In the method for producing the second monolith, the internal volume of a reaction vessel is not particularly limited provided that the monolith intermediate (2) may be accommodated in the reaction vessel. The monolith intermediate (2) may be placed either in a reaction vessel that accommodates the monolith intermediate (2) with a clearance therearound or in a reaction vessel that accommodates the monolith intermediate (2) with no clearance therearound, when viewed from the above. Of these, a reaction vessel in which the thick monolith after polymerization can be placed with no clearance therearound and without being pressed by the inner wall of the vessel may not distort the monolith and is efficient because the reaction raw material is not wasted. Even if the reaction vessel has a large internal volume and a clearance around the monolith after polymerization, the vinyl monomers and crosslinking agent are adsorbed on or distributed in the monolith intermediate (2). Thus, no particle aggregate structure is formed in the clearance portion in the reaction vessel.

In the step III according to the method for producing the second monolith, the monolith intermediate (2) is brought into a state that the intermediate (2) is impregnated with the mixture (solvent) in the reaction vessel. The mixture obtained in the step II and the monolith intermediate (2) is preferably blended such that the amount of the vinyl monomer added is 3 to 50 times by weight, preferably 4 to 40 times by weight the amount of the monolith intermediate (2). This makes it possible to obtain a second monolith having a thick skeleton and a moderate opening diameter. The vinyl monomers and the crosslinking agent in the mixture in the reaction vessel are adsorbed on or distributed in the skeleton of the monolith intermediate in a stationary state, and polymerization proceeds inside the skeleton of the monolith intermediate (2).

In the step III according to the method for producing the second monolith, various conditions for polymerization are selected depending on the type of the monomers and the type of the initiator. For example, when 2,2'-azobis(isobutyronitrile), 2,2'-azobis(2,4-dimethylvaleronitrile), benzoyl peroxide, lauroyl peroxide, potassium persulfate, or the like is used as the initiator, the mixture may be polymerized with heating in a sealed vessel at 30 to 100° C. for 1 to 48 hours in an inert atmosphere. By polymerizing with heating the vinyl monomers and the crosslinking agent adsorbed on or distributed in the skeleton of the monolith intermediate (2) are polymerized inside the skeleton to thereby thicken the skeleton. After completion of polymerization, the content is removed and extracted with a solvent such as acetone to remove unreacted vinyl monomers and the organic solvent to obtain a second monolith.

A second monolith ion exchanger can be obtained by performing a step IV of introducing ion exchange groups into the second monolith as the thick organic porous body obtained in the step III.

Ion exchange groups are introduced into the second monolith in the same manner as the method for introducing ion exchange groups into the first monolith.

Although having a markedly large opening diameter, the second monolith and second monolith ion exchanger have high mechanical strength because of having a thick skeleton.

<Description of Third Monolith and Third Monolith Ion Exchanger>

A third monolith ion exchanger includes a bicontinuous structure that comprises a three-dimensionally continuous skeleton comprising an aromatic vinyl polymer that has a crosslinked structural unit content of 0.1 to 5.0 mol % based on all constituent units and having an average thickness of 1 to 60 μm in a dry state, and three-dimensionally continuous holes defined by the skeleton having an average diameter of 10 to 200 μm in a dry state, the third monolith ion exchanger having ion exchange groups, a total pore volume of 0.5 to 10 mL/g in a dry state, and an ion exchange capacity per weight in a dry state of 1 to 6 mg equivalents/g, and the ion exchange groups being uniformly distributed in the organic porous ion exchanger. A third monolith, which is a monolith before ion exchange groups are introduced, is an organic porous body including a bicontinuous structure that comprises a three-dimensionally continuous skeleton comprising an aromatic vinyl polymer that has a crosslinked structural unit content of 0.1 to 5.0 mol % based on all constituent units and having an average thickness of 1 to 60 μm in a dry state, and three-dimensionally continuous holes defined by the skeleton having an average diameter of 10 to 200 μm in a dry state, the organic porous body having a total pore volume in a dry state of 0.5 to 10 mL/g.

Figure 4:
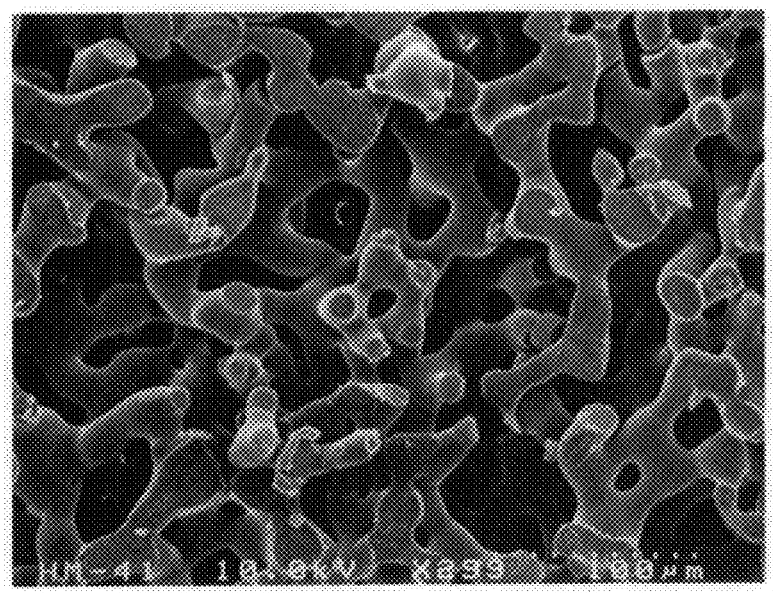
FIG. 4 is a SEM photograph of an exemplary embodiment of a third monolithic organic porous cation exchanger.
Figure 5:
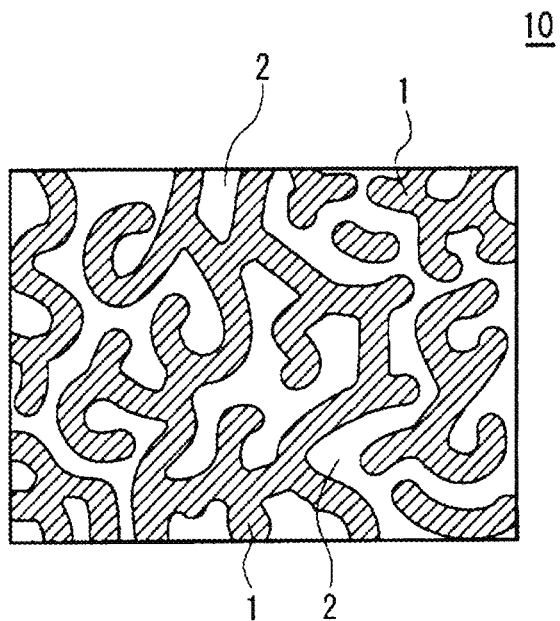
FIG. 5 is a schematic view showing a bicontinuous structure of the third monolithic organic porous cation exchanger.

The third monolith ion exchanger includes a bicontinuous structure that comprises a three-dimensionally continuous skeleton having an average thickness of 1 to 60 μm, preferably 3 to 58 μm in a dry state, and three-dimensionally continuous holes defined by the skeleton having an average diameter of 10 to 200 μm, preferably 15 to 180 μm, particularly preferably 20 to 150 μm in a dry state. FIG. 4 shows a SEM photograph of an exemplary embodiment of the third monolith ion exchanger, and FIG. 5 shows a schematic view of the bicontinuous structure of the third monolith ion exchanger. The bicontinuous structure, as shown in the schematic view of FIG. 5, is a structure 10 in which a continuous skeleton phase 1 and a continuous hole phase 2 are entangled with each other and three-dimensionally continued together. The continuous holes 2 have higher continuity of holes and a more uniform size of the holes, as compared with those of conventional open-cell type monoliths and particle-agglomeration type monoliths. Additionally, the monolith has higher mechanical strength due to its thick skeleton.

An average diameter of the three-dimensionally continuous holes of less than 10 μm in a dry state is not preferable because the pressure loss upon liquid passage increases. An average diameter exceeding 200 µm is not preferable because the organic solvent insufficiently contacts the monolith ion exchanger and, as a result, the efficiency of removing polyvalent metal ions becomes insufficient. An average thickness of the skeleton of less than 1 µm in a dry state is not preferable because the monolith ion exchanger is significantly deformed especially upon liquid passage at a high flow rate. Furthermore, an average thickness of the skeleton of less than 1 µm in a dry state is not preferable because the contact efficiency between the organic solvent and the monolith ion exchanger is reduced, and thus the efficiency of removing polyvalent metal ions is reduced. In contrast, a thickness of the skeleton exceeding 60 µm is not preferable because the skeleton is excessively thickened, and thus the pressure loss upon liquid passage increases.

The average diameter of the openings of the third monolith in a dry state, the average diameter of the openings of the third monolith ion exchanger in a dry state, and the average diameter of the openings of a third monolith intermediate (3) in a dry state to be obtained in the step I of production of third monolith described below are measured by mercury porosimetry and each indicate the maximal value of a pore distribution curve obtained by mercury porosimetry. The average thickness of the skeleton of the third monolith ion exchanger in a dry state is determined by SEM observation on the third monolith ion exchanger in a dry state. Specifically, the third monolith ion exchanger in a dry state is observed by a SEM at least three times. The thickness of the skeleton in the image obtained is measured, and the average value of them is taken as the average thickness. The skeleton has a rod-like shape and a circular cross-sectional shape, but may include an irregular cross-sectional shape such as an elliptical cross-sectional shape. In this case, the thickness is the average value of the minor axis and the major axis.

The total pore volume per weight of the third monolith ion exchanger in a dry state is 0.5 to 10 mL/g. A total pore volume of less than 0.5 mL/g is not preferable because the pressure loss upon liquid passage increases, and furthermore, because the amount of permeation per unit cross-sectional area is reduced, and thus the throughput is reduced. In contrast, a total pore volume exceeding 10 mL/g is not preferable because the mechanical strength decreases, causing a considerable deformation of the monolith ion exchanger especially upon liquid passage at a high flow rate. Furthermore, a total pore volume exceeding 10 mL/g is not preferable because the contact efficiency between the organic solvent and the monolith ion exchanger is reduced, and thus the efficiency of removing polyvalent metal ions is reduced. When the size and total pore volume of the three-dimensionally continuous holes are within the above range, the exchanger is in an extremely uniform contact with a reaction liquid, has a large contact area, and enables a liquid to pass under a low pressure loss.

In the third monolith ion exchanger, the material constituting the skeleton is an aromatic vinyl polymer that has a crosslinked structural unit content of 0.1 to 5 mol %, preferably 0.5 to 3.0 mol %, based on all constituent units and is hydrophobic. A crosslinked structural unit content of less than 0.1 mol % is not preferable because the mechanical strength is insufficient. In contrast, a crosslinked structural unit content exceeding 5 mol %, the structure of the porous body is likely to deviate from the bicontinuous structure. Examples of the type of the aromatic vinyl polymer include, but are not particularly limited to, polystyrene, poly(α-methylstyrene), polyvinyltoluene, polyvinylbenzyl chloride, polyvinyl biphenyl, and polyvinylnaphthalene. The above polymers may be polymers obtained by copolymerizing a single type of a vinyl monomer with a crosslinking agent, polymers obtained by polymerizing a plurality of vinyl monomers with a crosslinking agent, or blends of two or more polymers. Of these organic polymer materials, from the viewpoint of ease of formation of a continuous structure, ease of introduction of ion exchange groups, high mechanical strength, and excellent stability in acid or alkali, styrene-divinylbenzene copolymers and vinylbenzyl chloride-divinylbenzene copolymers are preferable.

The ion exchange groups introduced into the third monolith ion exchanger are the same as the ion exchange groups introduced into the first monolith ion exchanger.

The ion exchange groups introduced into the third monolith ion exchanger are uniformly distributed not only on the surface of the porous body but also inside the skeleton of the porous body.

The third monolith ion exchanger has an ion exchange capacity that is an ion exchange capacity per weight in a dry state of 1 to 6 mg equivalents/g. Since the third monolith ion exchanger has high continuity and uniformity of the three-dimensionally continuous holes, a decrease in the total pore volume may not significantly increase the pressure loss. Thus, the ion exchange capacity per volume can be dramatically increased while the pressure loss is suppressed low. When the ion exchange capacity per weight is in the range described above, the efficiency of removing polyvalent metal ions is improved. When the third monolith ion exchanger is a monolith anion exchanger, anion exchange groups have been introduced into the third monolith anion exchanger, and the anion exchange capacity per weight in a dry state is 1 to 6 mg equivalents/g. When the third monolith ion exchanger is a monolith cation exchanger, cation exchange groups have been introduced into the third monolith cation exchanger, and the cation exchange capacity per weight in a dry state is 1 to 6 mg equivalents/g.

<Method for Producing Third Monolith and Third Monolith Ion Exchanger>

The third monolith can be obtained by performing a step I of stirring a mixture of oil-soluble monomers including no ion exchange group, a surfactant, and water to prepare a water-in-oil emulsion and then polymerizing the water-in-oil emulsion to obtain a monolithic organic porous intermediate (hereinbelow, also referred to as the monolith intermediate (3)) including a continuous macropore structure having a total pore volume of more than 16 mL/g and 30 mL/g or less, a step II of preparing a mixture of aromatic vinyl monomers, 0.3 to 5 mol % of a crosslinking agent having at least two vinyl groups in one molecule in the total oil-soluble monomers, an organic solvent that dissolves the aromatic vinyl monomers and crosslinking agent but does not dissolve a polymer produced by polymerizing the aromatic vinyl monomer, and a polymerization initiator, and a step III of polymerizing the mixture obtained in the step II in a stationary state and in the presence of the monolith intermediate (3) obtained in the step I to obtain a third monolith as an organic porous body including a bicontinuous structure.

In the step I according to the method for producing the third monolith, the step I of obtaining a monolith intermediate (3) is only required to be carried out in compliance with the method described in Japanese Patent Laid-Open No. 2002-306976.

That is, in the step I according to the method for producing the third monolith, examples of the oil-soluble monomer including no ion exchange group include monomers that include no ion exchange group such as a carboxylic acid group, a sulfonic acid group, a tertiary amino group, and a quaternary ammonium group, have low solubility in water, and is lipophilic. Specific examples of these monomers include aromatic vinyl monomers such as styrene, α-methylstyrene, vinyltoluene, vinylbenzyl chloride, vinylbiphenyl, and vinylnaphthalene; α-olefins such as ethylene, propylene, 1-butene, and isobutene; diene monomers such as butadiene, isoprene, and chloroprene; halogenated olefins such as vinyl chloride, vinyl bromide, vinylidene chloride, and tetrafluoroethylene; nitrile monomers such as acrylonitrile and methacrylonitrile; vinyl esters such as vinyl acetate and vinyl propionate; and (meth)acrylic monomers such as methyl acrylate, ethyl acrylate, butyl acrylate, 2-ethylhexyl acrylate, methyl methacrylate, ethyl methacrylate, propyl methacrylate, butyl methacrylate, 2-ethylhexyl methacrylate, cyclohexyl methacrylate, benzyl methacrylate, and glycidyl methacrylate. Of these monomers, suitable examples include aromatic vinyl monomers such as styrene, α-methylstyrene, vinyltoluene, vinylbenzyl chloride, and divinylbenzene. These monomers may be used either singly or in combinations of two or more. Note that it is preferable to select a crosslinkable monomer, such as divinylbenzene or ethylene glycol dimethacrylate, as at least one component of oil-soluble monomers and set the content of the crosslinkable monomer to 0.3 to 5 mol %, preferably 0.3 to 3 mol % based on the total oil-soluble monomers because a bicontinuous structure is advantageously formed.

The surfactant used in the step I according to the method for producing the third monolith is the same as the surfactant used in the step I according to the method for producing the second monolith, and thus will not be elaborated upon.

In the step I according to the method for producing the third monolith, a polymerization initiator may be used as required when a water-in-oil emulsion is formed. As the polymerization initiator, a compound that generates radicals by heat or light irradiation is suitably used. The polymerization initiator may be water-soluble or oil-soluble, and examples thereof include 2,2'-azobis(isobutylonitrile), 2,2'-azobis(2,4-dimethylvaleronitrile), 2,2'-azobis(2-methylbutyronitrile), 2,2'-azobis(4-methoxy-2,4-dimethylvaleronitrile), dimethyl 2,2'-azobisisobutyrate, 4,4'-azobis(4-cyanovaleric acid), 1,1'-azobis(cyclohexane-1-carbonitrile), benzoyl peroxide, lauroyl peroxide, potassium persulfate, ammonium persulfate, tetramethylthiuram disulfide, hydrogen peroxide-ferrous chloride, and sodium persulfate-sodium hydrogen sulfite.

In the step I according to the method for producing the third monolith, a mixing method in which oil-soluble monomers including no ion exchange group, a surfactant, water, and a polymerization initiator are mixed to form a water-in-oil emulsion is the same as the mixing method in the step I according to the method for producing the second monolith, and will not be elaborated upon.

The monolith intermediate (3) obtained in the step I according to the method for producing the third monolith is an organic polymer material, preferably an aromatic vinyl polymer, having a crosslinked structure. The crosslink density of the polymer material is not particularly limited, and the crosslinked structural unit content is 0.1 to 5 mol %, preferably 0.3 to 3 mol % based on all constituent units constituting the polymer material. A crosslinked structural unit content of less than 0.3 mol % is not preferable because the mechanical strength is insufficient. In contrast, a content exceeding 5 mol % is not preferable because the structure of the monolith becomes likely to deviate from the bicontinuous structure. In particular, when the total pore volume is 16 to 20 mL/g, the crosslinked structural unit is preferable set to less than 3 mol % in order to form a bicontinuous structure.

In the step I according to the method for producing the third monolith, the type of polymer material for the monolith intermediate (3) is the same as the polymer material for the monolith intermediate (3) according to the method for producing the second monolith, and will not be elaborated upon.

Figure 6:
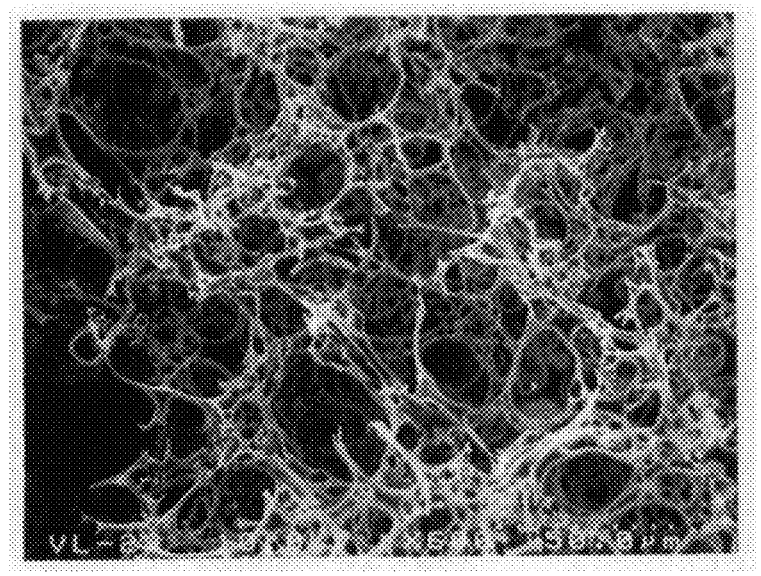
FIG. 6 is a SEM photograph of an exemplary embodiment of a monolith intermediate (3).

The monolith intermediate (3) obtained in the step I according to the method for producing the third monolith has a total pore volume per weight in a dry state of more than 16 mL/g and 30 mL/g or less, preferably more than 16 mL/g and 25 mL/g or less. That is, this monolith intermediate (3), which basically includes a continuous macropore structure, has significant large openings (mesopores), which are overlapping macropores, thus having a structure in which the skeleton constituting the monolith structure is similar as much as possible to a two-dimensional wall surface to a one-dimensional rod-like skeleton. FIG. 6 shows a SEM photograph of an exemplary embodiment of a monolith intermediate (3), which has a skeleton similar to a rod-like shape. When this monolith intermediate (3) is allowed to coexist in the polymerization system, a porous body including a bicontinuous structure is formed based on the structure of the monolith intermediate (3) as a mold. An excessively small total pore volume is not preferable because the structure of the monolith obtained after polymerization of the vinyl monomers changes from the bicontinuous structure to a continuous macropore structure. In contrast, an excessively large total pore volume is not preferable because the mechanical strength of the monolith obtained after polymerization of the vinyl monomers is reduced, or when ion exchange groups are introduced, the ion exchange capacity per volume is reduced. In order to bring the total pore volume of the monolith intermediate (3) to the above range, the ratio between the monomers and the water should be set to approximately 1:20 to 1:40.

The monolith intermediate (3) obtained in the step I according to the method for producing the third monolith has an average diameter of the openings (mesopores), which are overlapping macropores, of 5 to 100 μm in a dry state. An average diameter of the openings of less than 5 μm in a dry state is not preferable because the diameter of the openings of the monolith obtained after polymerization of the vinyl monomers becomes smaller, and thus the pressure loss upon fluid permeation increases. In contrast, an average diameter exceeding 100 μm is not preferable because the diameter of the openings of the monolith obtained after polymerization of the vinyl monomers excessively enlarges, and thus the organic solvent insufficiently contacts the monolith ion exchanger and, as a result, the efficiency of removing polyvalent metal ions is reduced. It is preferable that the monolith intermediate (3) has a uniform structure in which the macropores have a uniform size and the openings have a uniform diameter. Without limitation thereto, some non-uniform macropores that are larger than the uniform macropores may be interspersed in the uniform structure.

The step II according to the method for producing the third monolith is a step of preparing a mixture of aromatic vinyl monomers, 0.3 to 5 mol % of a crosslinking agent having at least two vinyl groups in one molecule in the total oil-soluble monomers, an organic solvent that dissolves the aromatic vinyl monomers and crosslinking agent but does not dissolve a polymer produced by polymerizing the aromatic vinyl monomers, and a polymerization initiator. Note that the steps I and II may be performed in any order and the step II may be performed before or after the step I.

The aromatic vinyl monomer used in the step II according to the method for producing the second monolith is not particularly limited provided that the aromatic vinyl monomer is a lipophilic aromatic vinyl monomer that includes a polymerizable vinyl group in the molecule and has high solubility in an organic solvent. It is preferable to select vinyl monomers used to produce a polymer material that is the same as or similar to the monolith intermediate (3) allowed to coexist in the above polymerization system. Specific examples of these vinyl monomers include styrene, α-methylstyrene, vinyltoluene, vinylbenzyl chloride, vinyl biphenyl, and vinylnaphthalene. These monomers may be used either singly or in combinations of two or more. Aromatic vinyl monomers suitably used are styrene, vinylbenzyl chloride, and the like.

The amount of the aromatic vinyl monomer added in the step II according to the method for producing the third monolith is 5 to 50 times by weight, preferably 5 to 40 times by weight the amount of the monolith intermediate (3) allowed to coexist upon polymerization. An amount of the aromatic vinyl monomer added of less than 5 times the amount of the monolith intermediate (3) is not preferable because it is not possible to thicken the rod-like skeleton and moreover, if ion exchange groups are introduced, the ion exchange capacity per volume after introduction of the ion exchange groups is reduced. In contrast, an amount of the aromatic vinyl monomer added exceeding 50 times is not preferable because the diameter of the continuous holes becomes smaller and the pressure loss upon liquid passage increases.

The crosslinking agent suitably used in the step II according to the method for producing the third monolith includes at least two polymerizable vinyl groups in the molecule, and has high solubility in an organic solvent. Specific examples of the crosslinking agent include divinylbenzene, divinylnaphthalene, divinylbiphenyl, ethylene glycol dimethacrylate, trimethylolpropane triacrylate, and butanediol diacrylate. These crosslinking agents may be used either singly or in combinations of two or more. A preferable crosslinking agent is an aromatic polyvinyl compound such as divinylbenzene, divinylnaphthalene, and divinylbiphenyl in respect of high mechanical strength and stability in hydrolysis. The amount of the crosslinking agent used is 0.3 to 5 mol %, particularly 0.3 to 3 mol %, based on the total amount of the vinyl monomer and the crosslinking agent (the total oil-soluble monomers). An amount of the crosslinking agent used of less than 0.3 mol % is not preferable because the mechanical strength of the monolith is insufficient. In contrast, an excessive amount is not preferable because, if ion exchange groups are introduced, it may be difficult to quantitatively introduce the ion exchange groups. The crosslinking agent is preferably used in an amount so as to achieve a crosslink density substantially equivalent to the crosslink density of the monolith intermediate (3) allowed to coexist upon polymerization of the vinyl monomers/crosslinking agent. If both the amounts used significantly differ from each other, the crosslink density may be unevenly distributed in the monolith produced and, if ion exchange groups are introduced, cracking of the monolith is likely to occur upon introduction reaction of ion exchange groups.

The organic solvent used in the step II according to the method for producing the third monolith is an organic solvent that dissolves the aromatic vinyl monomers and crosslinking agent but does not dissolve a polymer produced by polymerizing the aromatic vinyl monomers, that is, a poor solvent for a polymer produced by polymerizing the aromatic vinyl monomers. The organic solvent significantly depends on the type of the aromatic vinyl monomer, and thus it is difficult to give common specific examples. Examples of the organic solvent used when the aromatic vinyl monomer is styrene include alcohols such as methanol, ethanol, propanol, butanol, hexanol, cyclohexanol, octanol, 2-ethylhexanol, decanol, dodecanol, propylene glycol, and tetramethylene glycol; chain (poly)ethers such as diethyl ether, butyl cellosolve, polyethylene glycol, polypropylene glycol, and polytetramethylene glycol; chain saturated hydrocarbons such as hexane, heptane, octane, isooctane, decane, and dodecane; and esters such as ethyl acetate, isopropyl acetate, cellosolve acetate, and ethyl propionate. Even a good solvent for polystyrene such as dioxane, THF, and toluene may also be used as the organic solvent if the good solvent is used in a small amount together with the poor solvent described above. The organic solvent is preferably used in an amount such that the concentration of the above aromatic vinyl monomer is 30 to 80% by weight. A case in which the amount of the organic solvent used deviates from the above range to decrease the concentration of the aromatic vinyl monomer to less than 30% by weight is not preferable because the polymerization rate may be reduced or a monolith structure after polymerization may deviates from the range of the third monolith. In contrast, a concentration of the aromatic vinyl monomer exceeding 80% by weight is not preferable because polymerization may run away.

The polymerization initiator used in the step II according to the method for producing the third monolith is the same as the polymerization initiator used in the step II according to the method for producing the second monolith, and will not be elaborated upon.

The step III according to the method for producing the third monolith is a step of polymerizing the mixture obtained in the step II in a stationary state and in the presence of the monolith intermediate (3) obtained in the step I to change the continuous macropore structure of the monolith intermediate (3) to a bicontinuous structure to thereby obtain a third monolith as a bicontinuous structure monolith. The monolith intermediate (3) used in the step III serves an extremely important role in creating a monolith having a novel structure of the present invention. As disclosed in National Publication of International Patent Application No. 7-501140 and the like, a particle-agglomeration type monolithic organic porous body is obtained by statically polymerizing vinyl monomers and a crosslinking agent in a specific organic solvent in the absent of the monolith intermediate (3). In contrast, when the monolith intermediate (3) including a continuous macropore structure is allowed to exist in the above polymerization system as the third monolith, the structure of the monolith after polymerization dramatically changes, the particle aggregation structure disappears to thereby provide a third monolith having the aforementioned bicontinuous structure. The reason, although has not been elucidated in detail, may be considered as follows: in the absence of the monolith intermediate (3), a crosslinked polymer produced by polymerization is deposited and precipitated in the form of particles to form a particle aggregation structure. In contrast, in the presence of a porous body (intermediate) having a large total pore volume in the polymerization system, the vinyl monomers and crosslinking agent are, from the liquid phase, adsorbed on or distributed in the skeleton portion of the porous body, and polymerization proceeds inside the porous body. Then, the skeleton constituting the monolith structure changes from a two-dimensional wall surface to a one-dimensional rod-like skeleton so as to form the third monolith having a bicontinuous structure.

In the method for producing the third monolith, the internal volume of the reaction vessel is the same as the description of the internal volume of the reaction vessel according to the method for producing the second monolith, and will not be elaborated upon.

In the step III according to the method for producing the third monolith, the monolith intermediate (3) is brought into a state that the intermediate (3) is impregnated with the mixture (solvent) in the reaction vessel. The mixture obtained in the step II and the monolith intermediate (3) is preferably blended such that the amount of the aromatic vinyl monomer added is 5 to 50 times by weight, preferably 5 to 40 times by weight the amount of the monolith intermediate (3). This makes it possible to obtain a third monolith including a bicontinuous structure that has three-dimensionally continuous holes of a moderate size and a three-dimensionally continuous thick skeleton. The aromatic vinyl monomers and the crosslinking agent in the mixture in the reaction vessel are adsorbed on or distributed in the skeleton of the monolith intermediate (3) in a stationary state, and polymerization proceeds inside the skeleton of the monolith intermediate (3).

The polymerization conditions for the step III according to the method for producing the third monolith is the same description of the polymerization conditions for the step III according to the method for producing the second monolith, and will not be elaborated upon. The third monolith is obtained by performing the step III.

A third monolith ion exchanger is obtained by performing a step IV of introducing ion exchange groups into the third monolith obtained in the step III.

Ion exchange groups are introduced into the third monolith in the same manner as the method for introducing ion exchange groups into the first monolith.

Although having a markedly large size of the three-dimensionally continuous holes, the third monolith and third monolith ion exchanger have high mechanical strength because of having a thick skeleton. Additionally, having a thick skeleton, the third monolith ion exchanger can have a high ion exchange capacity per volume in a dry state and furthermore, enables a reaction liquid to pass for a long period at a high flow rate under low pressure.

Then, in the method for purifying an organic solvent of the present invention, an organic solvent is purified by contacting the organic solvent containing polyvalent metal ions with a monolithic organic porous ion exchanger to remove the polyvalent metal ions in the organic solvent.

In the method for purifying an organic solvent of the present invention, the method for contacting an organic solvent containing polyvalent metal ions with a monolithic organic porous ion exchanger is not particularly limited, and an example of the method is a method comprising filling a treating tower or column with a monolithic organic porous ion exchanger, and then, continuously supplying an organic solvent to the treating tower or column filled with the monolithic organic porous ion exchanger while discharging the organic solvent from the treating tower or column to thereby continuously contact the organic solvent containing polyvalent metal ions with the monolithic organic porous ion exchanger. In the case of continuously supplying an organic solvent to the treating tower or column filled with the monolithic organic porous ion exchanger while discharging the organic solvent from the treating tower or column, the organic solvent may be allowed to pass the treating tower or column through in the top-to-bottom direction or the bottom-to-top direction. When a column is used, the column may be placed laterally, and an organic solvent may be allowed to pass laterally through the column.

Examples of the method for filling a treating tower with the monolithic organic porous ion exchanger include a method in which the monolithic organic porous ion exchanger is cut into about 5-mm squares and a treating tower is filled with the cut monolithic organic porous ion exchanger by feeding the exchanger thereto and a method in which monolithic organic porous bodies are accumulated and arranged in a honeycomb form. Alternatively, an example of the method for filling a column with the monolithic organic porous ion exchanger is a method in which a column is filled by packing a monolithic organic porous ion exchanger having an outer diameter slightly larger than the inner diameter of the column into the column. The column material is not particularly limited provided that the material is resistant to organic solvents and does not contaminate such an organic solvent. Preferable examples thereof include polyolefinic materials such as polyethylene and polypropylene and fluorine materials such as polyfluoroalkoxy resin (PFA) and polytetrafluoroethylene resin (PTFE). When the column material is a metal material such as SUS and hastelloy, a column the inside of which is coated with a polyolefinic material or fluorine material is used as a metallic column. As for a treating tower, which is made of metal such as SUS and hastelloy, treating towers the inside of which is coated with a polyolefinic material or a fluorine material are used. In any filling method, it is preferable to fill the treating tower or column with a monolithic organic porous ion exchanger so as to prevent a short path of the organic solvent. Alternatively, a panel strip may be attached to the outlet side or to each of the outlet and inlet sides of the direction of passage of the organic solvent through the treating tower or column to thereby support the monolithic organic porous ion exchanger in the treating tower or column. The panel strip material is preferably the same as the material of the treating tower or column.

In the method for purifying an organic solvent of the present invention, when the organic solvent containing polyvalent metal ions is contacted with the monolithic organic porous ion exchanger by continuously supplying the organic solvent before treatment to the treating tower filled with the monolithic organic porous ion exchanger while discharging the organic solvent after treatment from the treating tower, the liquid passage speed of the organic solvent, as a space velocity (SV), is preferably 1 to 1000 $h^{-1}$, particularly preferably 2 to 100 $h^{-1}$. A liquid passage speed of the organic solvent exceeding the above range is not preferable because the liquid passage resistance increases or the liquid passage speed excessively increases relative to the adsorption rate for metal components, and thus polyvalent metal ions become insufficiently adsorbed. In contrast, a liquid passage speed of less than the above range, the treatment speed becomes excessively low. Alternatively, in the method for purifying an organic solvent of the present invention, after the organic solvent is once contacted with the monolithic organic porous ion exchanger, the organic solvent can be again contacted with the monolithic organic porous ion exchanger.

In the method for purifying an organic solvent of the present invention, the temperature when the organic solvent containing polyvalent metal ions is contacted with the monolithic organic porous ion exchanger is not particularly limited and preferably 0 to 70° C., particularly preferably 15 to 40° C.

The method for purifying an organic solvent of the present invention can satisfactorily remove polyvalent metal ions, of which removal has been difficult with particulate ion exchange resin. When an organic solvent, as a liquid to be treated, contains monovalent metal ions such as lithium ions, sodium ions, and potassium ions, the method also can satisfactorily remove these monovalent metal ions.

High-purity organic solvents thus obtained by carrying out the method for purifying an organic solvent of the present invention are suitably used as organic solvents for drying semiconductor substrates after washing with water, as solvents for solution polymerization of a resist material or the like, and for organic-solvent washing of resist stripping after pattern formation or the like in semiconductor manufacturing processes.

The present invention is specifically described below by way of examples, which are merely exemplary and are not intended to limit the present invention.

EXAMPLES

Reference Example 1

Production of First Monolith Cation Exchanger (Production of First Monolith)

Mixed and uniformly dissolved were 19.2 g of styrene, 1.01 g of divinylbenzene, 2.25 g of sorbitan monooleate (hereinafter abbreviated as SMO), and 0.05 g of 2,2'-azobis (isobutyronitrile). The styrene/divinylbenzene/SMO/2,2'-azobis(isobutyronitrile) mixture was then added to 180 g of pure water and stirred under reduced pressure using a vacuum mixing and degassing mixer as a planetary stirrer (manufactured by EME CORPORATION) to obtain a water-in-oil emulsion. The emulsion was immediately transferred into a reaction vessel. After sealing the reaction vessel, the emulsion was polymerized in a stationary state at 60° C. for 24 hours. After completion of polymerization, the content was removed, extracted with methanol, and then dried under reduced pressure to produce a monolith having a continuous macropore structure. The internal structure of the first monolith A thus obtained was observed by a SEM. As a result, the monolith had an open-cell structure, and the openings (mesopores) in the overlapping macropores had an average diameter of 13 μm and a total pore volume of 8.4 mL/g, as measured by mercury porosimetry.

(Production of First Monolith Cation Exchanger)

The first monolith A produced by the method described above was placed in a column-type reactor and allowed to react at 20° C. for three hours by allowing a solution of 500 g of chlorosulfonic acid and 4 L of dichloromethane to pass through the reactor. After the reaction was completed, methanol was added into the system to quench the unreacted chlorosulfonic acid followed by further washing with methanol, and a product was removed. The product was washed with pure water in the end to thereby obtain a first monolith cation exchanger A.

The first monolith cation exchanger A obtained had a cation exchange capacity in a dry state of 4 mg equivalents/g, and it was confirmed that sulfonic acid groups were quantitatively introduced. As determined from measurement by mercury porosimetry, the monolith cation exchanger had an average diameter of three-dimensionally continuous holes in a dry state of 13 μm and a total pore volume in a dry state of 8.4 mL/g.

Subsequently, in order to confirm the distribution state of sulfonic acid groups in the first monolith cation exchanger A, the distribution state of sulfur was observed by an EPMA. From the distribution state of sulfur in the skeleton cross section, it was possible to confirm that sulfur was uniformly distributed not only on the surface of the skeleton but also inside the skeleton of the monolith cation exchanger, and thus sulfonic acid groups were uniformly introduced into the monolith cation exchanger.

Reference Example 2

Production of Third Monolith Cation Exchanger (Production of Monolith Intermediate (3) (Step I))

Mixed and uniformly dissolved were 9.28 g of styrene, 0.19 g of divinylbenzene, 0.50 g of sorbitan monooleate (SMO), and 0.25 g of 2,2'-azobis(isobutyronitrile). The styrene/divinylbenzene/SMO/2,2'-azobis(isobutyronitrile) mixture was then added to 180 g of pure water and stirred under reduced pressure using a vacuum mixing and degassing mixer as a planetary stirrer (manufactured by EME CORPORATION) to obtain a water-in-oil emulsion. The emulsion was immediately transferred into a reaction vessel. After sealing the reaction vessel, the emulsion was polymerized in a stationary state at 60° C. for 24 hours. After completion of polymerization, the content was removed, extracted with methanol, and then dried under reduced pressure to produce a monolith intermediate (3) B having a continuous macropore structure. The internal structure of the monolith intermediate (dry body) thus obtained was observed by a SEM. As a result, the wall section defining two adjacent macropores was extremely thin and rod-like, but the monolith intermediate had an open-cell structure. The openings (mesopores) in the overlapping macropores had an average diameter of 40 μm and a total pore volume of 18.2 mL/g, as measured by mercury porosimetry.

(Production of Third Monolith)

Subsequently, 216.6 g of styrene, 4.4 g of divinylbenzene, 220 g of 1-decanol, and 0.8 g of 2,2'-azobis(2,4-dimethylvaleronitrile) were mixed and uniformly dissolved (step II). The above monolith intermediate was then placed in a reaction vessel and immersed in the styrene/divinylbenzene/1-decanol/2,2'-azobis(2,4-dimethylvaleronitrile) mixture. After degassing the mixture in a decompression chamber, the reaction vessel was sealed. The mixture was then polymerized in a stationary state at 50° C. for 24 hours. After completion of polymerization, the content was removed, Soxhlet-extracted with acetone, and then dried under reduced pressure (step III) to obtain a third monolith B.

The internal structure of the third monolith B (dry body) containing 1.2 mol % of a crosslinked component comprising the styrene/divinylbenzene copolymer thus obtained was observed by a SEM. As a result, the monolith included a bicontinuous structure in which the skeleton and the holes each three-dimensionally continued and both the phases were entangled with each other. The skeleton had an average thickness of 20 μm, which was measured from the SEM image. The monolith had an average diameter of the three-dimensionally continuous holes of 70 μm and a total pore volume of 4.4 mL/g, as measured by mercury porosimetry. Note that the average diameter of the holes is the maximal value of a pore distribution curve obtained by mercury porosimetry.

(Production of Third Monolith Cation Exchanger)

The monolith produced by the method described above was placed in a column-type reactor and allowed to react at 20° C. for three hours by allowing a solution of 500 g of chlorosulfonic acid and 4 L of dichloromethane to pass through the reactor. After the reaction was completed, methanol was added into the system to quench the unreacted chlorosulfonic acid followed by further washing with methanol, and a product was removed. The product was washed with pure water in the end to thereby obtain a third monolith cation exchanger B.

The monolith cation exchanger obtained had a cation exchange capacity in a dry state of 4.7 mg equivalents/g, and it was confirmed that sulfonic acid groups were quantitatively introduced. When the internal structure of the second monolith cation exchanger B was also observed by a SEM, the monolith cation exchanger included a bicontinuous structure in which the skeleton and the holes each three-dimensionally continued and both the phases were entangled with each other. The skeleton had an average thickness in a dry state of 20 μm, which was measured from the SEM image. As determined from measurement by mercury porosimetry, the monolith cation exchanger had an average diameter of three-dimensionally continuous holes in a dry state of 70 μm and a total pore volume in a dry state of 4.4 mL/g.

Subsequently, in order to confirm the distribution state of sulfonic acid groups in the second monolith cation exchanger B, the distribution state of sulfur was observed by an EPMA. It was possible to confirm that sulfur was uniformly distributed not only on the surface of the skeleton but also inside the skeleton of the monolith cation exchanger, and thus sulfonic acid groups were uniformly introduced into the monolith cation exchanger.

(Particulate Ion Exchange Resin)

As particulate ion exchange resin, particulate cation exchange resin a (manufactured by ORGANO CORPORATION, Amberjet, average particle size: 500 μm, cation exchange capacity: 4 mg equivalents/g) was provided.

Example 1

A column having an internal volume of 50 mL and an inner diameter of 16 mm was filled with 40 mL of the first monolith cation exchanger A obtained as described above, and then, 12% hydrochloric acid was allowed to pass through the column. The column was then washed with ultrapure water followed by replacing the moisture by isopropanol.

Subsequently, isopropanol containing metals in the content shown in Table 1 was allowed to pass through the column at 25° C. (room temperature) at a liquid passage speed of SV 50 h$^{-1}$. The metal content of the treatment liquid obtained was measured using ICP-MS. The results are shown in Table 1.

Comparative Example 1

The procedure was carried out in the same manner as in Example 1 except that 40 mL of the first monolith cation exchanger A was replaced by 40 mL of the particulate cation exchange resin a. The results are shown in Table 1.

Example 2

The procedure was carried out in the same manner as in Example 1 except that the liquid passage speed was changed from SV 50 h$^{-1}$ to SV 4 h$^{-1}$. The results are shown in Table 1.

Comparative Example 2

The procedure was carried out in the same manner as in Example 1 except that 40 mL of the first monolith cation exchanger A was replaced by 40 mL of particulate cation exchange resin a and that the liquid passage speed was changed from SV 50 h$^{-1}$ to SV 4 h$^{-1}$. The results are shown in Table 1.

TABLE 1

| SV (h$^{-1}$) | Example 1 50 | | Comparative Example 1 50 | | Example 2 4 | | Comparative Example 2 4 | |
|---|---|---|---|---|---|---|---|---|
| | Before treatment | After treatment | Before treatment | After treatment | Before treatment | After treatment | Before treatment | After treatment |
| Li | <50 | <50 | <50 | <50 | <50 | <50 | <50 | <50 |
| Na | 859 | <50 | 1276 | <50 | 588 | <50 | 772 | <50 |
| Mg | 100 | <50 | 73 | 65 | 97 | <50 | 161 | <50 |
| Al | 94 | <50 | 42 | <50 | 428 | <50 | 747 | <50 |
| K | 148 | <50 | 438 | <50 | 260 | <50 | 215 | <50 |
| Ca | 611 | <50 | 967 | <50 | 524 | <50 | 984 | <50 |
| Cr | 12294 | 1396 | 17916 | 17799 | 2817 | <50 | 4628 | 1545 |
| Mn | <50 | <50 | <50 | <50 | <50 | <50 | <50 | <50 |
| Fe | 157 | <50 | 52 | <50 | 585 | <50 | <50 | <50 |
| Co | <50 | <50 | <50 | <50 | <50 | <50 | <50 | <50 |
| Ni | <50 | <50 | <50 | <50 | 142 | <50 | <50 | <50 |
| Cu | <50 | <50 | <50 | <50 | <50 | <50 | <50 | <50 |
| Zn | 123 | <50 | 349 | 81 | 131 | <50 | 200 | <50 |
| Cd | <50 | <50 | <50 | <50 | <50 | <50 | <50 | <50 |
| Pb | <50 | <50 | <50 | <50 | <50 | <50 | <50 | <50 |

REFERENCE SIGNS LIST

1 Skeleton phase
2 Hole phase
10 Bicontinuous structure
11 Rectangular image area
12 Skeleton portion appearing in cross section
13 Macropore

The invention claimed is:

1. A method for purifying an organic solvent, comprising contacting an organic solvent containing at least any one or two or more of a magnesium ion, a chromium ion, and a zinc ion with a monolithic organic porous cation exchanger, wherein the monolithic organic porous cation exchanger comprises a continuous skeleton phase and a continuous hole phase, the exchanger has a thickness of a continuous skeleton of 1 to 100 μm, an average diameter of continuous holes of 1 to 1000 μm, a total pore volume of 0.5 to 50 mL/g, and a cation exchange capacity per weight in a dry state of 1 to 6 mg equivalents/g, and cation exchange groups are uniformly distributed in the organic porous cation exchanger, and wherein the liquid passage speed of the organic solvent to the monolithic organic porous cation exchanger as a space velocity (SV), is 2 to 100 $h^{-1}$.

2. The method for purifying an organic solvent according to claim 1, wherein the organic solvent is any one or two or more of alcohols, cellosolves, ethers, ketones, and esters, or a mixture of two or more of alcohols, cellosolves, ethers, ketones, and esters.

3. The method for purifying an organic solvent according to claim 1, wherein the organic solvent is isopropanol.

4. The method for purifying an organic solvent according to claim 1, wherein the monolithic organic porous ion exchanger comprises an open-cell structure in which cellular macropores overlap and the overlapping macropores form openings having an average diameter of 1 to 1000 μm, the exchanger has a total pore volume of 1 to 50 mL/g and an ion exchange capacity per weight in a dry state of 1 to 6 mg equivalents/g, and ion exchange groups are uniformly distributed in the organic porous ion exchanger.

5. The method for purifying an organic solvent according to claim 1, wherein the monolithic organic porous ion exchanger comprises a continuous macropore structure in which cellular macropores overlap and the overlapping macropores form openings having an average diameter of 30 to 300 μm, the exchanger has a total pore volume of 0.5 to 10 mL/g, and an ion exchange capacity per weight in a dry state of 1 to 6 mg equivalents/g, and ion exchange groups are uniformly distributed in the organic porous ion exchanger, and an area of a skeleton portion appearing in cross section in a SEM image of a cut section of the continuous macropore structure (dry body) is 25 to 50% based on the image area.

6. The method for purifying an organic solvent according to claim 1, wherein the monolithic organic porous ion exchanger comprises a bicontinuous structure that comprises a three-dimensionally continuous skeleton comprising an aromatic vinyl polymer that has a crosslinked structural unit content of 0.1 to 5.0 mol % based on all constituent units including ion exchange groups introduced and having an average thickness of 1 to 60 μm, and three-dimensionally continuous holes defined by the skeleton having an average diameter of 10 to 200 μm, the exchanger has a total pore volume of 0.5 to 10 mL/g and an ion exchange capacity per weight in a dry state of 1 to 6 mg equivalents/g, and the ion exchange groups are uniformly distributed in the organic porous ion exchanger.

* * * * *